(12) United States Patent
Orellana-Tavra et al.

(10) Patent No.: US 11,083,795 B2
(45) Date of Patent: Aug. 10, 2021

(54) AMORPHOUS METAL-ORGANIC FRAMEWORKS

(71) Applicant: Cambridge Enterprise Limited, Cambridge (GB)

(72) Inventors: Claudia Orellana-Tavra, Cambridge (GB); Nigel Slater, Cambridge (GB); David Fairen-Jimenez, Cambridge (GB); Michelle Teplensky, Cambridge (GB); Emma Baxter, Cambridge (GB); Thomas Bennett, Cambridge (GB); Anthony Cheetham, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 23 days.

(21) Appl. No.: 15/735,145

(22) PCT Filed: Jun. 24, 2016

(86) PCT No.: PCT/EP2016/064746
§ 371 (c)(1),
(2) Date: Dec. 8, 2017

(87) PCT Pub. No.: WO2016/207397
PCT Pub. Date: Dec. 29, 2016

(65) Prior Publication Data
US 2018/0147284 A1    May 31, 2018

(30) Foreign Application Priority Data

Jun. 24, 2015  (GB) .................................... 1511125

(51) Int. Cl.
| | |
|---|---|
| *A61K 47/24* | (2006.01) |
| *A61K 31/19* | (2006.01) |
| *A61K 31/277* | (2006.01) |
| *A61K 31/352* | (2006.01) |
| *A61K 31/513* | (2006.01) |
| *A61K 31/713* | (2006.01) |
| *C07F 9/94* | (2006.01) |
| *C07F 7/00* | (2006.01) |
| *A61K 47/12* | (2006.01) |

(52) U.S. Cl.
CPC .............. *A61K 47/24* (2013.01); *A61K 31/19* (2013.01); *A61K 31/277* (2013.01); *A61K 31/352* (2013.01); *A61K 31/513* (2013.01); *A61K 31/713* (2013.01); *A61K 47/12* (2013.01); *C07F 7/003* (2013.01); *C07F 9/94* (2013.01)

(58) Field of Classification Search
CPC ...... A61K 47/24; A61K 31/19; A61K 31/277; A61K 31/352; A61K 31/513; A61K 31/713; A61K 47/12; C07F 9/94
USPC ........................................................ 514/183
See application file for complete search history.

(56) References Cited

PUBLICATIONS

Bennett et al. (ChemCommum, 2011, 47, 7983-7985) (Year: 2011).*
Zhu et al. (Chem. Commun., 2014, 50, 8779-8782) (Year: 2014).*
Bennett et al. (Accounts of Chemical Research 2014, 47, 1555-1562; (Year: 2014).*
Nicolaides Applied catalysis A: General, 1999, 185, 211-217 (Year: 1999).*
Yan et al., Journal of chromatography A, 2018, 1542, 19-27 (Year: 2018).*
Bennett et al., (2011) Reversible pressure-induced amorphization of a zeolitic imidazolate framework (ZIF-4) Chemical Communications—Chemcom. 47(28): 7983-7985.
Bennett et al., (2011) "Facile Mechanosynthesis of Amorphous Zeolitic Imidazolate Frameworks," Journal of the American Chemical Society,133: 14546-14549.
Bennett et al., (2013) "Ball-Milling-Induced Amorphization of Zeolitic Imidazolate Frameworks (ZIFs) for the Irreversible Trapping of Iodine," Chemistry A European Journal 19: 7049-7055.
Bennett et al., (2014) "Amorphous Metal-Organic Framworks," Accounts of Chemical Research 47(5): 1555-1562.
Bernini et al., (2014) "Screening of bio-compatible metal-organic frameworks as potential drug carriers using Monte Carlo simulations," Journal of Materials Chemistry B 2: 766-774.
Bertz et al., (2013) "Encapsulation of proteins in hydrogel carrier systems for controlled drug delivery: Influence of network structure and drug size on release rate," Journal of Biotechnology, 163: 243-249.
Cavka et al., (2008) "A New Zirconium Inorganic Building Brick Forming Metal Organic Frameworks with Exceptional Stability," Journal of the American Chemical Society, 130: 13850-13851.
Chapman et al., (2011) "Trapping Guests within a Nanoporous Metal-Organic Framework through Pressure-Induced Amorphization," Journal of the American Chemical Society, 133(46): 18583-18585.
Cunha et al., (2013) "Rational of Drug Encapsulation and Release from Biocompatible Porous Metal-Organic Frameworks," Chemistry of Materials, 25(14): 2767-2776.

(Continued)

*Primary Examiner* — Yevgeny Valenrod
(74) *Attorney, Agent, or Firm* — Rudy J. Ng; Bozicevic, Field & Francis LLP

(57) ABSTRACT

The invention provides an amorphous metal-organic framework for use in methods of treatment. The amorphous metal-organic framework may hold a component for delivery. The amorphous metal-organic framework is obtained or is obtainable by amorphization of a crystalline amorphous metal-organic framework holding the component. The amorphous metal-organic framework may be a zirconium-containing or a bismuth-containing metal-organic framework, such as a framework having arylcarboxylate ligands, such as benzenedicarboxylate ligands.

20 Claims, 12 Drawing Sheets

(56) References Cited

PUBLICATIONS

Cunha et al., (2013) "Rationalization of the entrapping of bioactive molecules into a series of functionalized porous zirconium terephthalate MOFs†," Journal of Materials Chemistry B, 1: 1101-1108.

Della Rocca et al., (2011) "Nanoscale Metal-Organic Frameworks for Biomedical Imaging and Drug Delivery," Accounts of Chemical Research, 44(10): 957-968.

Erttmann et al., (1988) "Pharmacokinetics of doxorubicin in man: dose and schedule dependence," Journal Cancer Research Clinical Oncology, 114: 509-513.

Gimenez-Marques et al., (2016) "Nanostructured metal-organic frameworks and bio-related applications," Coordination Chemistry Reviews, 307(12): 342-360.

Greim (1999) "Zirconium and its compounds," The MAK Collection for Occupational Health and Safety 224-236.

He et al., (2014) Nanoscale Metal-Organic Frameworks for the Co-Delivery of Cisplatin and Pooled siRNAS to Enhance Therapeutic Efficacy in Drug-Resistant Ovarian Cancer Cells, Journal of the American Chemical Society, 136: 5181-5184.

Horcajada et al., (2010) "Porous metal-organic-framework nanoscale carriers as a potential platform for drug lelivery and imaging," Nature Materials, 9(2): 172-178.

Horcajada et al., (2012) "Metal-Organic Frameworks in Biomedicine," Chemical Reviews 112: 1232-1268.

Huang et al., (2009) "Preparation of core-shell biodegradable microfibers for long-term drug delivery," Journal of Biomedical Materials Research Part A, 90: 1243-1251.

Javadi et al., (2013) "Ultrasonic gene and drug delivery using eLiposomes," Journal of Controlled Release, 167: 92-100.

Jin-Gou et al., (2012) "Preparation, Characterization of Hydrophobic Drug in Combine Loaded Chitosan/Cyclodextrin/Trisodium Citrate Nanoparticles and in Vitro Release Study," Chem. Res. Chinese Universities, 28: 166-170.

Katz et al., (2013) "A facile synthesis of UiO-66, UiO-67 and their derivatives," Chem. Commun., 49: 9449-9451.

Keskin and Kizilel (2011) "Biomedical Applications of Metal Organic Frameworks," Industrial & Engineering Chemistry Research, 50: 1799-1812.

Kung et al., (2013) "Metal-Organic Framework Thin Films Composed of Free-Standing Acicular Nanorods Exhibiting Reversible Electrochromism," Chemistry of Materials, 25: 5012-5017.

Lim et al., (2013) "One-step fabrication of core-shell structured alginate-PLGA/PLLA microparticles as a novel drug delivery system for water soluble drugs," Biomaterials Science, 1: 486-493.

Mckinlay et al., (2008) "Exceptional Behavior over the Whole Adsorption-Storage-Delivery Cycle for NO in Porous Metal Organic Frameworks," Journal of the American Chemical Society, 130(31): 10440-10444.

Meng et al., (2012) "Single walled carbon nanotubes as drug delivery vehicles: Targeting doxorubicin to tumors ," Biomaterials, 33: 1689-1698.

Mondloch et al., (2013) "Vapor-Phase Metalation by Atomic Layer Deposition in a Metal-Organic Framework," Journal of the American Chemical Society 135: 10294-10297.

Oliver et al., (2004) "Loading Human Mesencgymal Stem Cells with Trehalose by Fluid-Phase Endocytosis," Cell Preservation Technology, 2(1): 35-49.

Orellana-Tavra et al., (2015) "Amorphous metal-organic frameworks for drug delivery," Chem. Commun., 51: 13878-13881.

Rieter et al., (2008) "Nanoscale Coordination Polymers for Platinum-Based Anticancer Drug Delivery," Journal of the American Chemical Society, 130(35): 11584-11585.

Shan et al., (1996) "Anthracycline-Induced Cardiotoxicity," American College of Physicians, 125: 47-58.

Sharp et al., (2013) "Amphipathic polymer-mediated uptake of trehalose for dimethyl sulfoxide-free human cell cryopreservation," Cryobiology, 67: 305-311.

Su et al., (2015) "Compression-Induced Deformation of Individual Metal-Organic Framework Microcrystals," Journal of the American Chemical Society, 137(5): 1750-1753.

Tamames-Tabar et al., (2014) "Cytotoxicity of nanoscaled metal-organic frameworks," Journal of Materials Chemistry B 2: 262-271.

Whitehead et al., (2009) "Knocking down barriers: advances in siRNA delivery," Nature Reviews Drug Discovery, 8:129-138.

Xie et al., (2013) "Capture and conversion of CO2 at ambient conditions by a conjugated microporous polymer," Nature Communications, 4: 1-7.

Zhou et al., (2011) "Amorphization of Metal-Organic Framework Mof-5 by Electrical Discharge," Plasma Chemistry and Plasma Processing, Kluwer Academic Publishers-Plenum Publishers, NE 31(3): 499-506.

ISR and WO for PCT/EP2016/064746 dated Sep. 26, 2016 pp. 1-17.
Search Report for GB 1511125.5 dated Mar. 18, 2016 pp. 1-5.

\* cited by examiner

AMORPHOUS METAL-ORGANIC FRAMEWORKS

The work leading to this invention has received funding from the European Research Council under the European Union's Seventh Framework Programme (FP7/2007-2013)/ERC grant agreement no. 227781

RELATED APPLICATION

The present case claims priority to, and the benefit of, GB 1511125.5 filed on 24 Jun. 2015, the contents of which are hereby incorporated by reference in their entirety.

FIELD OF THE INVENTION

The invention provides amorphous metal-organic frameworks and their use in methods of treatment. Also provided are methods of preparing the amorphous metal-organic frameworks and methods for delivering a component from an amorphous metal-organic framework.

BACKGROUND

Methods of medical treatment typically make use of bioactive compounds. Whilst a compound may possess biological activity, it may nevertheless not be ideally suited for use in therapy. For example a compound may suffer from poor solubility and non-selective biodistribution, which often results in the damage of healthy tissues and cardiotoxic effects (see Meng et al.; Erttmann et al. and Shan et al.).

A drug delivery system (DDS) may overcome these issues by improving the solubility of the bioactive compound, protecting the active agent from degradation, controlling the release of the bioactive in vivo, providing targeted delivery, and reducing toxic side effects.

Finding an effective drug delivery system for therapeutic agents has been an ongoing challenge in bioengineering. Recently, metal-organic frameworks (MOFs) have emerged as candidates for use in a drug delivery system owing to their useful chemical and physical characteristics. For example, metal-organic frameworks are known to have high pore volumes, large surface areas, multiple topologies and tunable pore size and surface chemistry (see Keskin et al. and Horcajada et al.).

Metal-organic frameworks are prepared by self-assembly processes from metal ions or metal clusters, which act as coordination centres for interconnection with organic ligands. The resulting products have a well-defined crystalline structure.

Metal-organic frameworks are able to encapsulate active agents by efficiently adsorbing them into their pore structures. For example, Horcajada et al. have loaded different anticancer and antiviral agents into metal-organic frameworks; Morris et al. have encapsulated and delivered the vasodilator agent nitric oxide gas (NO) from a metal-organic framework; He et al. have reported the use of metal-organic frameworks for the co-delivery of the anticancer cisplatin and small interference RNA, to enhance therapeutic effect. Here, the siRNA is apparently coordinated to metal sites on the exterior surface. The interior porosity of the metal-organic framework is apparently not used for loading in this situation.

Compared with other organic (e.g. liposomes and micelles) and inorganic (e.g. zeolites and mesoporous silicas) drug delivery systems, metal-organic frameworks have high loading capacities and the framework may be readily functionalized to enhance the affinity for the bioactive, and to allow the framework to target specific cell types.

The present inventors have recently described a computational screening study, the results of which showed that metal-organic frameworks are capable of encapsulating up to 2 grams of a bioactive per gram of the porous solid framework. This is a higher loading capacity than those loading capacities reported for mesoporous silicas and organic carriers: such are said to have maximum capacities of 0.25 to 0.30 mg of drug per mg of material (see Bernini et al. and Jin-gou et al.).

The industrial use of metal-organic frameworks has often been limited by the relatively poor stability of the frameworks. Furthermore, within the context of drug delivery systems, metal-organic frameworks present very fast kinetic deliveries for the encapsulated bioactive. For example, see Cunha et al. who describe the rapid release of caffeine from a MIL-53 metal-organic framework. The rapid release of a bioactive compound is not always desirable within a clinical setting, and a controlled, sustained and slow release of the active agent may be more appropriate.

Cunha et al. have also described the use of crystalline zirconium-based metal-organic frameworks based on UiO-66 to entrap caffeine and ibuprofen.

The present inventors have established that amorphous forms of metal-organic frameworks may be used to deliver components into the intracellular environment. The inventors have found that the release of the component is controlled, sustained and relatively slow, and the release may be the same or with greater control than the release of the component from the corresponding crystalline form.

SUMMARY OF THE INVENTION

In a general aspect, the invention provides an amorphous metal-organic framework and its use in methods of medical treatment. The amorphous metal-organic framework holds a component, such as a biologically active agent, and this component is releasable from the amorphous metal-organic framework.

The inventors have established that an amorphous metal-organic framework is capable of releasing the held component over a sustained period of time. Moreover, the relative instability of the amorphous metal-organic framework is advantageous in a drug delivery system, as the framework is easily biodegraded in vivo during and after release of the active agent. The amorphous metal-organic framework is also capable of transport across a cell membrane and accordingly the metal-organic framework may be used to deliver a component held within the framework into the intracellular space. This feature of the metal-organic framework is especially useful for delivering components that have poor solubility and/or are impermeable to the cell membrane.

The ability of the amorphous metal-organic framework to release a component is at least comparable to that of the crystalline form of the amorphous metal-organic framework, and in many cases the amorphous form of the metal-organic framework can provide an altered release profile when compared to that of the crystalline form. Indeed, in many cases the amorphous form can provide a longer period of release, a longer period of constant release, and/or may avoid the problem of burst release in the crystalline form.

Accordingly in a first aspect of the invention there is provided an amorphous metal-organic framework holding a component, optionally wherein the component is not molecular iodine ($I_2$), such as wherein the component has a molecular weight that is at least 100.

In one embodiment, the component has one or more carbon atoms and/or three or more atoms.

The amorphous metal-organic framework is obtained or is obtainable from a crystalline metal-organic framework holding a component. The crystalline metal-organic framework may be ball-milled, thereby to provide the amorphous metal-organic framework. Alternatively the crystalline metal-organic framework may be heat treated, thereby to provide the amorphous metal-organic framework.

In one embodiment, the metal-organic framework is a zirconium-containing metal-organic framework, for example a metal-organic framework having zirconium oxo-clusters. Additionally or alternatively, the metal-organic framework is a bismuth-containing metal-organic framework.

In one embodiment, the component is an active agent for use in a method of medical treatment.

In one embodiment, the amorphous metal-organic framework is provided within an aqueous mixture.

In a second aspect of the invention there is provided a pharmaceutical composition comprising an amorphous metal-organic framework holding a component, optionally provided together with one or more pharmaceutically acceptable ingredients, wherein the component is an active agent for use in a method of medical treatment.

In a third aspect of the invention there is provided an amorphous metal-organic framework, or a pharmaceutical composition comprising the amorphous metal-organic framework, for use in a method of medical treatment, wherein the amorphous metal-organic framework holds a component and the component is an active agent for use in a method of medical treatment.

In a fourth aspect of the invention there is provided an amorphous metal-organic framework or a pharmaceutical composition comprising the amorphous metal-organic framework, for use in a method of treating a proliferative disease, such as cancer, such as cervical cancer.

In a fifth aspect of the invention there is provided an amorphous metal-organic framework, or a pharmaceutical composition comprising the amorphous metal-organic framework, for use in a method of medical treatment, wherein the amorphous metal-organic framework holds a component and the component is an active agent for use in a method of medical treatment, and the method of treatment comprises the sustained release of the component from the amorphous metal-organic framework, such as the release of substantially all of the component over a period of at least 1 day, such as at least 2 days, such as at least 4 days, such as at least 7 days.

In a sixth aspect of the invention there is provided a method for preparing an amorphous metal-organic framework according to the first aspect of the invention, the method comprising the step of amorphizing a crystalline metal-organic framework holding a component.

In one embodiment the crystalline metal-organic framework is amorphized by ball-milling. Alternatively the crystalline metal-organic framework may be heat treated.

In one embodiment, the method comprises the preliminary step of preparing a crystalline metal-organic framework holding a component, the method comprising mixing a crystalline metal-organic framework with a component, thereby to yield the crystalline metal-organic framework holding a component.

In a seventh aspect of the invention there is provided a method of delivering a component to a target location, the method comprising the steps of:

(i) providing an amorphous metal-organic framework at a target location, wherein the amorphous metal-organic framework holds a component; and
(ii) permitting the release of the component from the amorphous metal-organic framework, thereby to provide the component at the target location.

In one embodiment, the target location is an intracellular location.

In one embodiment, the target location method is ex vivo.

In one embodiment, the target location is an extracellular location.

These and other aspects and embodiments of the invention are described in detail below.

DETAILED DESCRIPTION OF THE INVENTION

Figure 1:
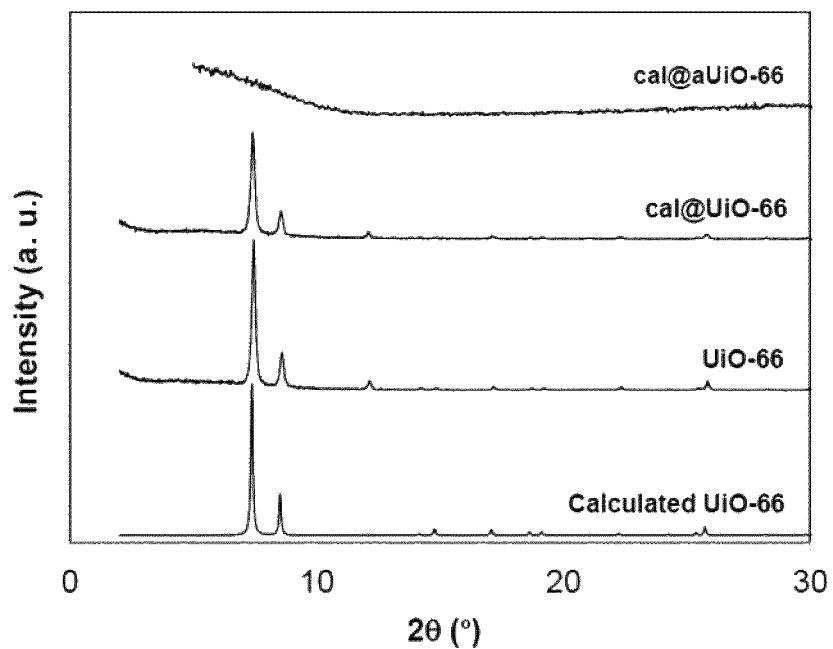
FIG. 1 shows the PXRD patterns of synthesized crystalline UiO-66 (pattern, second from bottom), crystalline calcein-loaded UiO-66 (cal@UiO-66, second from top) and amorphous calcein-loaded UiO-66 (cal@aUiO-66, top), together with the PXRD pattern calculated for crystalline UiO-66 (bottom).

The invention provides an amorphous metal-organic framework holding a component, and the use of this metal-organic framework in methods of treatment. The component may be a therapeutic agent for use in treatment.

Bennett et al. (*Chem.-Eur. J.*, 2013, 19, 7049) have previously described the preparation of amorphous metal-organic frameworks holding molecular iodine. The incorporation of the iodine into the framework was studied, as was its subsequent release. Iodine was adsorbed into a crystalline framework, which was subsequently collapsed by ball milling. The authors found that the molecular iodine was entrapped in the porosity of the framework.

The amorphous metal-organic frameworks described by Bennett et al. are used in a gas-solid interphase, and there is no suggestion that amorphous metal-organic frameworks could be used in a biological environment, such as an intercellular environment or an intracellular environment.

Bennett et al. describe the adsorption of the molecular iodine inside the porosity of the metal-organic framework. The molecular iodine was releasable from the metal-organic framework under conditions where the solid metal-organic framework was heated, for example a ZIF-8 framework was heated at 200° C. for at least 3 hours.

Furthermore, Bennett et al. do not show or suggest that an amorphous metal-organic framework can be used to deliver a component held within the framework to an intracellular location. Bennett et al. also do not describe the controlled, sustained and relatively slow release of a component from an amorphous metal-organic framework.

The amorphous metal-organic frameworks of the present invention are suitable for holding and subsequently releasing components of greater complexity than molecular iodine. As shown in the worked examples of the present case, an amorphous metal-organic framework may be used to deliver a relatively large, organic molecule—calcein—into an intracellular space.

Bennett et al. only disclose the use of iodine as a component to be loaded into an amorphous metal-organic framework. There is no suggestion that the amorphous metal-organic framework could be used to encapsulate therapeutically active agents, nor is there any suggestion that such agents could be released in a controlled fashion. Indeed, Bennett et al. actually suggest that an amorphous metal-organic framework could be used to sequester and permanently store harmful guest species (including radioactive iodine). This teaches away from the use of amorphous metal-organic frameworks for encapsulating and subsequently releasing components as part of a targeted delivery strategy.

Bennett et al. (*Chem. Commun.* 2011, 47, 7983) have also described the amorphization of ZIF-4. The properties of the amorphous material are not studied or considered, and there is no suggestion that the framework could or should hold a component for delivery, and there is certainly no suggestion that the framework should hold a therapeutic agent.

Bennett et al. refer to the presence of small molecules within the pores of the framework. However, these are molecules of a pressure transmitting fluid (PTF), and examples include methanol/ethanol. Such are added to the crystalline starting material and are present during the amorphization procedure. The authors look at the changes in the amorphous structure with the change in size of the PTF molecules.

Rieter et al. (*J. Am. Chem. Soc.* 2008, 130, 11584) describes the use of a nonporous nanoscale coordination polymer to hold and deliver a cis-platin type anticancer drug. The system described by Reiter et al. consists of Tb ions linked by DSCP, a functionalised cis-platin ligand. This is later encapsulated with silica in order to stabilise the formed particles. In this system the drug for delivery forms part of the ligand holding the network together. In contrast, the amorphous metal-organic frameworks for use in the present invention hold a component, such as a drug, within the pores of the framework.

Furthermore, the nanoscale coordination polymer is not obtained by amorphization of a crystalline metal-organic framework. Rather, the nanoscale coordination polymer is generated by precipitation of the ligand and metal precursors.

Chapman et al. (*J. Am. Chem. Soc.* 2011, 133, 18583) describe the amorphization of ZIF-8, and the use of the amorphized ZIF-8 to hold molecular iodine ($I_2$). The work in the paper is limited to the capture and release of iodine, and there is no evidence to show that ZIF-8 could and would work with more complex compounds.

Zhuo et al. (*Plasma Chem. Plasma Process* 2011, 31, 499) discuss processes for the amorphization of MOF-5, a zinc-based framework having benzenedicarboxylate. There is no suggestion anywhere in this document that MOF-5 could or should be used to hold and deliver an active agent. The authors simply describe a new method for amorphization of MOF-5, using electrical discharge. Zhuo et al. explain that electrical discharge appears to destroy parts of the ligand during the amorphization process. In contrast, the amorphization procedures described in the present case, such as ball-milling and temperature amorphization, do not alter the chemical functionality of the metal-organic framework. The effect of the amorphization is to collapse the pores in the structure, and not to alter the chemical structure of the ligands.

The present inventors have previously suggested in Giménez-Marqués et al. (*Coordination Chem. Rev.* 2016, 307, 342) that it is difficult to determine general rules for the release of drugs from metal-organic frameworks, and the release of each drug must be studied for each delivery condition for a given metal-organic framework. However, in the present work, the inventors have unexpectedly shown that different amorphous metal-organic frameworks are capable of releasing a component in a delayed manner, and additionally some systems are capable of releasing the component in a highly controlled manner also. In many cases the amorphous form is capable of delaying release to a greater extent than the corresponding crystalline form.

Metal-Organic Framework

The invention provides an amorphous metal-organic framework holding a component. The amorphous metal-organic framework is obtained or is obtainable from a crystalline metal-organic framework holding the component. The physical and chemical features of the crystalline metal-organic framework, and the amorphization process will therefore determine the physical and chemical features of the amorphous metal-organic framework.

A crystalline metal-organic framework is a network solid in which inorganic centres (or nodes) are connected by organic ligands. The inorganic centres may be metal ions or metal clusters. Within the crystalline metal-organic framework the inorganic centres are provided in a highly regular and extended arrangement. The crystalline framework is said to possess long range order.

Where a crystalline metal-organic framework holds a component, this component may be provided within the pores of the framework. Additionally, component may also be provided on the surface of the framework, meaning the external surface of the crystalline metal-organic framework.

It is preferred that the majority, such as substantially all, of the component is provided within the pores of the framework.

An amorphous metal-organic framework is obtainable from a crystalline metal-organic framework by disruption of the long range order. The process of amorphization (such as described in further detail below) is intended to introduce aperiodicity into the framework, thereby disrupting the long range order.

The change from long range order to disorder is observable in the X-ray diffraction patterns, where diffuse scattering in the amorphous framework results in the loss of the Bragg reflections that are observable in the crystalline framework. Thus, the X-ray diffraction pattern for an amorphous metal-organic framework does not contain discernible Bragg peaks.

The process of amorphization causes an irreversible collapse of the porous networks of the crystalline framework around the component that is held within the pores. Thus, the component is partially entrapped within the amorphous form of the framework. The inventors have established that this partial entrapment results in the prolonged controlled release of the component from the amorphous framework. The release of the component from the amorphous framework is believed to be controlled by partial material degradation (that is, dissolution of the framework) as well as diffusion of the component through the remaining porous network.

The crystalline metal-organic framework from which the amorphous framework is prepared is chosen for its suitability to hold the component. Thus, the pores of the crystalline metal-organic framework should be capable of holding the component within. Furthermore the pores of the crystalline framework must be accessible to the component, and it follows that the gates to the pores should be of a size to permit the component to pass into the pore.

If the gate and pore sizes are not sufficiently large, the component will not be taken up into the porosity of the crystalline metal-organic framework. Instead, the inventors have found that the component will be adsorbed onto the external surface of the framework. In this situation, the amorphization of the crystalline metal-organic framework does not entrap the component within. When the component is present on the surface of the amorphous metal-organic framework it is released rapidly from the framework.

Whether a component is entrapped within a framework or is simply adsorbed onto the external surface may be established by analytical means, or by studying the release kinetics of the component from the amorphous metal-organic framework.

Analysis of a crystalline metal-organic framework by XRD can show whether a component is present within the pores of the framework. For example, the presence of the component on the external surface may supress the XRD signals for the crystalline metal-organic framework itself.

As noted above, where the component is entrapped, its release from the amorphous framework with be relatively slow compared with the crystalline framework. Where the component is adsorbed onto the external surfaces, its release from the amorphous framework will be rapid and comparable to the release of the component the crystalline framework. In some instances the release from the amorphous framework may even be more rapid than the crystalline framework.

A metal-organic framework for use in the present invention typically contains a transition metal, an alkali metal, an alkaline earth metal and/or a post-transition metal. In one embodiment, metal-organic frameworks contain one or more transition metals. A metal-organic framework for use in the present invention may contain a metal that is selected from the group consisting of zirconium, zinc, cobalt, nickel, palladium, platinum, copper, indium, iron, bismuth, magnesium and potassium, and mixtures thereof. A metal-organic framework for use in the present invention may contain a metal that is selected from the group consisting of zirconium, zinc, cobalt, nickel, palladium, platinum, copper, indium and iron, and mixtures thereof. Additionally or alternatively the metal-organic framework may contain bismuth as a metal.

Typically a metal-organic framework contains only a single type of metal.

A metal may be present in the framework as a metal cluster, such as a metal oxo-cluster.

An example of a zirconium-containing metal-organic framework is UiO-66, which is exemplified in the present case, NU-1000 and NU-901. UiO-66 is $Zr_6O_4(OH)_4(BDC)_6$, where BDC is 1,4-benzenedicarboxylate. NU-1000 and NU-901 have the structure $Zr_6(\mu_3-OH)_8(OH)_8(TBAPy)_2$ where TBAPy is 1,3,6,8-tetrakis(p-benzoic acid)pyrene, where there is a difference in the channel shape between the NU-1000 and NU-901 frameworks, with the former having hexagonal-shaped channels and the latter having diamond-shaped channels. NU-1000 consists of an octahedral $Zr_6$ cluster, where eight of the twelve edges are connected to TBAPy, and the remaining coordination sites are capped by eight terminal —OH ligands.

Examples of zinc-containing metal-organic frameworks includes ZIF-1, ZIF-3, ZIF-4, MOF-5 and MOF-177.

An example of a cobalt-containing metal-organic framework is Co-ZIF-4.

Examples of nickel-, palladium-, platinum-, and copper-containing metal-organic frameworks include nickel(II) bisimidazolate, palladium(II) bisimidazolate, platinum(II) bisimidazolate, and copper(II) bisimidazolate respectively.

An example of a magnesium-containing metal-organic framework is CPO-27.

An example of a potassium-containing metal-organic framework is CDMOF-1.

An example of a bismuth-containing metal-organic framework is CAU-7. In the crystal structure of CAU-7, $Bi^{3+}$ ions are nine-fold coordinated by oxygen atoms provided by $BTB^{3-}$ ions (1,3,5-benzenetrisbenzoic acid ions), thereby forming threefold capped trigonal prisms. Face sharing of the $BiO_9$ polyhedral leads to chains along the c-axis.

In one embodiment, the metal in the metal-organic framework has an oral lethal dose of at least 0.5 g/kg, at least 1.0 g/kg, at least 2.0 g/kg, or at least 10 g/kg in a rat model, for example as measured in a salt form.

In one embodiment, the metal-organic framework is a zirconium-based organic framework. Zirconium-based systems are particularly attractive as zirconium low toxicity. For example, the oral lethal dose for zirconyl acetate, determined as $LD_{50}$, is around 4.1 g/kg in a rat model. Furthermore, the human body contains around 300 mg of zirconium, and the amount of zirconium ingested daily is typically around 3.5 mg/day. Indeed there is a daily requirement for Zr at 0.05 mg per day.

The inventors have found that a crystalline zirconium-based organic framework UiO-66 has measured $IC_{50}$ values on HeLa cells of about 1.50 and 1.36 mg/mL over 24 and 48 hours respectively.

In one embodiment, a crystalline or amorphous metal-organic framework has an $IC_{50}$ of at least 0.1, at least 0.5, at least 1.0, or at least 1.5 mg/mL as measured against a test cell line, such as HeLa cells.

Methods for measuring $IC_{50}$ values are described in the present case, and are well known in the art.

The framework has organic ligands connected to the metal centres. The organic ligands for use in the metal-organic framework are typically aryl-containing ligands, which may be carboaryl and heteroaryl-containing ligands.

The ligand may include a heteroaryl group such as imidazolyl or pyridyl.

The ligand may include a phenyl group.

The ligand may contain multiple aryl groups, and these may be the same or different. For example, the ligand may contain two phenyl groups. The aryl groups may be bonded to each other, such as in a biphenyl group.

In one embodiment, the ligand may comprise a fused aromatic ring system, such as a pyrene group, or such as a naphthyl group.

An aryl ring, where present, may be substituted, for example with carboxy (COOH or $COO^-$), alkyl, haloalkyl, hydroxyl, halo and/or nitro substituent groups may be present. Preferably, an aryl ring is substituted with one or more carboxy groups.

Suitable alternative organic ligands are well known in the art.

In one embodiment, the ligand has one or two aryl groups. Here, an aryl group may be a phenyl group or a fused aromatic group, such as a naphthyl group. Where two aryl groups are present, these may be present as a biaryl group, such as a biphenyl group, within the ligand. In one embodiment, the ligand has one aryl group. Here, the aryl group may be a phenyl group or a fused aromatic groups, such as a naphthyl group.

In one embodiment, the organic ligand is a phenyl-containing ligand. The phenyl group may be substituted, such as disubstituted with a carboxy group, and optionally further substituted. In one embodiment, the organic ligand is benzenedicarboxylate, such as 1,4-benzenedicarboxylate, where the benzene ring is optionally further monosubstituted with —$NH_2$, —$NO_2$, —Cl, —Br, —COOH (or —$COO^-$) or —$CH_3$, or is optionally further disubstituted with —$CF_3$, —$CH_3$ or —OH. The use of ligands of this type is described by Cunha et al.

In one embodiment, each organic ligand is a benzenedicarboxylate ligand independently selected from the group consisting of BDC, BDC—Cl, BDC—Br, BDC—$NH_2$, BDC—$CH_3$, BDC—$(OH)_2$, BDC—$(CO_2H)_2$ and BDC—$(CF_3)_2$, where BDC is 1,4-benzenedicarboxylate. Where the ring is disubstituted, for example disubstituted with —$CF_3$, the substituents are provided in a para-arrangement (1,4-arrangment).

Alternatively, each organic ligand is selected from a ligand shown below:

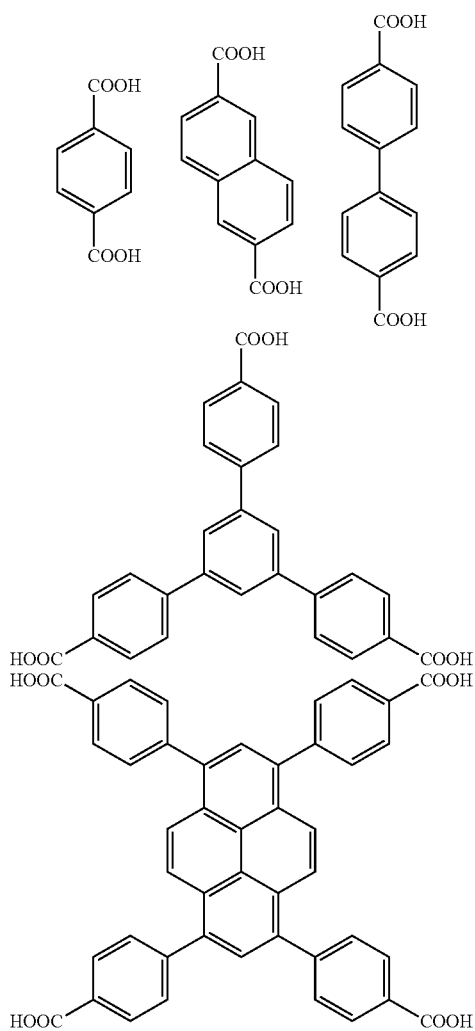

where an aryl group may be optionally further substituted with NH$_2$, —NO$_2$, —Cl, —Br, —COOH (or —COO$^-$) or —CH$_3$, or is optionally further disubstituted with —CF$_3$, —CH$_3$ or —OH, and the salt forms thereof.

Alternatively, each organic ligand is selected from a ligand shown below:

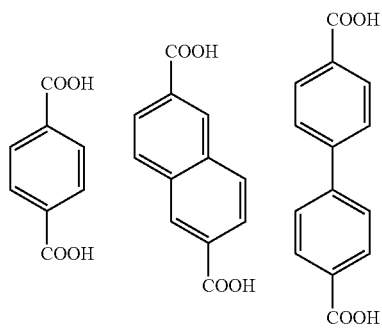

where an aryl group may be optionally further substituted with NH$_2$, —NO$_2$, —Cl, —Br, —COOH (or —COO$^-$) or —CH$_3$, or is optionally further disubstituted with —CF$_3$, —CH$_3$ or —OH, and the salt forms thereof.

Preferably, each organic ligand is selected from a ligand shown below:

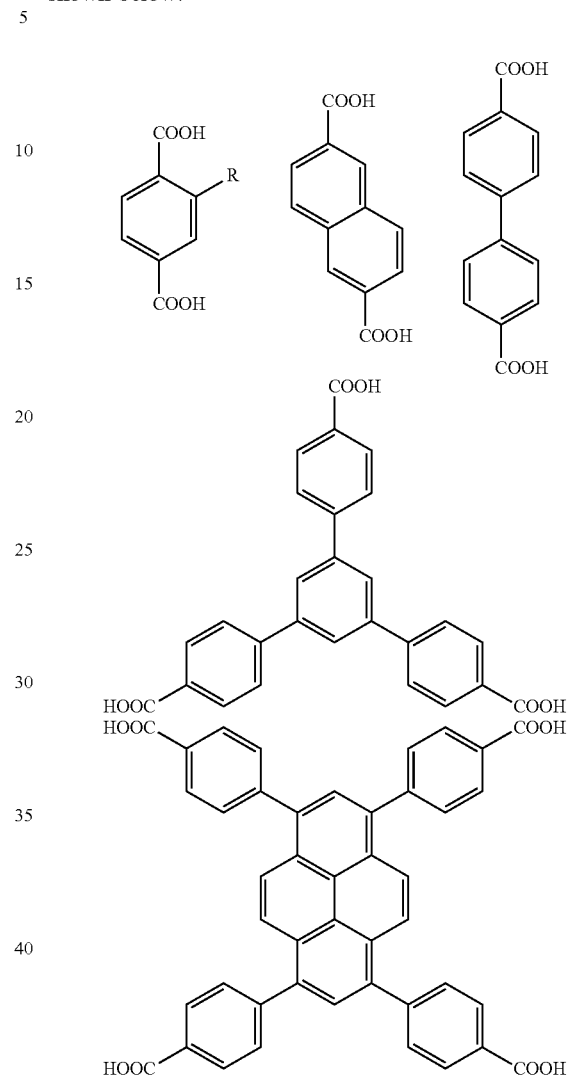

where R is selected from —H, —Br, —NO$_2$, and —NH$_2$, and the salt forms thereof.

More preferably, such as wherein the metal-organic framework is a zirconium-containing framework, each organic ligand is selected from a ligand shown below:

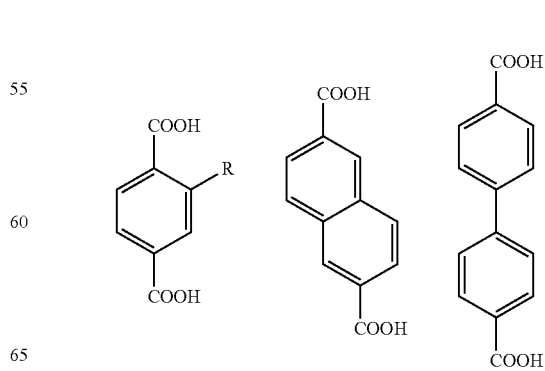

where R is selected from —H and —NH$_2$, and the salt forms thereof.

The use of organic ligands having a carboxylate group is particularly favourable in applications where the amorphous metal-organic framework is degraded under physiological conditions. The pKa value of carboxylate-containing organic ligands, such as the organic linker 1,4-benzenedicarboxylate, is typically <5.5. At physiological pH—about 7.4—it is said that the deprotonation of the carboxylate-containing organic ligand is easier (compared with neutral conditions), and the complexing power of the ligand for the metal centre is accordingly reduced (see, for example, Horcajada et al.).

It is typically the case that the amorphous metal-organic frameworks of the invention are stable in deionized water at ambient temperatures (such as a temperature of 25° C., at neutral pH).

The organic ligand typically also has low toxicity. In one embodiment, the organic ligand in the metal-organic framework has an oral lethal dose of at least 0.5 g/kg, at least 1.0 g/kg, at least 2.0 g/kg, or at least 10 g/kg in a rat model.

In one embodiment, the metal-organic framework is a zirconium-based organic framework having a $Zr_6$ cluster core, for example having $Zr_6$-octahedra. The cluster core may be a $Zr_6O_4(OH)_4$ cluster.

The $Zr_6$ cluster core may include O and OH groups, for example μ3-O and μ3-OH capping groups. The $Zr_6$ cluster core may have polyhedron edges bridged by the organic ligands. In one embodiment, the metal-organic framework is selected from UiO-66, NU-1000 and NU-901.

In one embodiment, the metal-organic framework is UiO-66.

In one embodiment, the metal-organic framework is $Zr_6O_4(OH)_4(BDC)_6$, where BDC is 1,4-benzenedicarboxylate.

The space group of the crystalline metal-organic framework is not particularly limited.

The crystalline metal-organic framework may be provided in the form of particles, such as nanoparticles.

The size of the particle is important for determining whether or not the particle is capable of passing into a cell, through the cell wall, such as an eukaryotic cell wall. Larger particles are prevented from passing through the cell wall, or their progress is sufficiently impeded as to make their use as cell delivery agents impractical. Smaller particles are also capable of freely circulating through the smallest capillaries within a subject.

In one embodiment, the average largest dimension of a particle is at most 200, at most 250, at most 300, at most 400, or at most 500 nm.

Alternatively, the average largest dimension of a particle is at 1 μm, at most 5 μm, or at most 10 μm. In one embodiment, the average largest dimension of a particle is at least 10, at least 50, at least 100, or at least 150 nm, or at least 200 nm.

In one embodiment, the average largest dimension of a particle is within a range having the upper and lower limits selected from the values given above. For example, average largest dimension of a particle is selected from the range 50 to 300 nm, such as 100 to 200 nm. In a further example the average largest dimension of a particle is selected from the range 50 nm to 5 μm, such as 100 to 5 μm.

Particle sizes may be determined from the SEM images of a sample of a metal-organic framework. Exemplary SEM methods are described herein.

Typically, the particles of the crystalline metal-organic framework have a low size distribution. In contrast, the particles of the amorphous metal-organic framework have a large size distribution.

For example, the relative standard deviation for the particles of the crystalline metal-organic framework is at most 10%, such as at most 5%, for example at most 2%. The worked examples in the present case describe the preparation of crystalline UiO-66 having a relative standard deviation of 4.58% (262±12 nm).

The relative standard deviation for the particles of the amorphous metal-organic framework may be at least 15%, such as at least 25%, for example at least 50%. The worked examples in the present case describe the preparation of amorphous UiO-66 having a relative standard deviation of 57.7% (272±157 nm).

The crystalline metal-organic framework has a large porosity, such as a large surface area and large pore volume. In one embodiment, the crystalline metal-organic framework has a specific surface area (SBET) that is at least 500, at least 700, at least 1,000, at least 1,100 or at least 1,200 m$^2$ g$^{-1}$.

The specific surface area may be determined in the usual way, using nitrogen adsorption at 77 K. An exemplary SBET method is described herein and is also described by Cunha et al.

In one embodiment, the crystalline metal-organic framework has a specific pore volume that is at least 0.10, at least 0.20, at least 0.40 or at least 0.50 cm$^3$ g$^{-1}$. The specific pore volume may be determined by nitrogen adsorption at 77 K in the usual way. Such methods are described by Cunha et al.

In one embodiment, the crystalline metal-organic framework has a density of metal atoms, expressed as the number of tetrahedral vertices per unit volume, that is at most 2.5, at most 2.6, at most 3.0, at most 3.5, or at most 5.0 n/m$^3$.

In one embodiment, the crystalline metal-organic framework has a density of metal atoms, expressed as the number of tetrahedral vertices per unit volume, that is at least 1.5, at least 2.0, at least 2.1 or at least 2.2 n/m$^3$.

The crystal density may be determined from the X-ray crystal data.

The references to specific pore volume and specific surface area may apply to a crystalline metal-organic framework holding a component, or the crystalline metal-organic framework without the component present. It is expected that the specific pore volume and specific surface area values for the amorphous metal-organic framework will differ, perhaps significantly, from those values determined for the crystalline metal-organic framework.

In the amorphous form of the metal-organic framework the pore volume and surface area will be minimal.

The crystalline metal-organic framework contains cavities and such may be accessed via gates (or windows) in the framework. In the crystalline metal-organic framework for use in the present invention, cavities within the framework may have a largest cross section (Ø) of at least 5, at least 6, at least 7, at least 8, at least 9 or at least 10 Å. Gates in the framework may have a largest cross section (Ø) of at least 3, at least 4, at least 5, at least 6, at least 7, or at least 8 Å, and the largest cross section of the gates is typically less than the largest cross section of the cavity.

The metal-organic framework holds a component. The component may be present at an amount of at least 0.5 wt %, at least 1 wt %, at least 2 wt % or at least 4 wt %.

In one embodiment, the component is present at an amount of at most 10 wt %, at most 15 wt %, at most 20 wt %, at most 25 wt %, at most 35 wt %, at most 50 wt %, or at most 65 wt %. In one embodiment, the component is present at an amount of at most 30 wt %. For example, Cunha et al. describe the crystalline metal-organic framework UiO-66 holding caffeine or ibuprofen at amounts in the range 10 to 25 wt %.

The preferences above may apply when the component has a relatively small molecular weight, such as 2,000 or less, such 1,000 or less, such as 500 or less.

Alternatively, the component is present at an amount of at most 0.5 wt %, at most 1 wt %, at most 2 wt % or at most 4 wt %.

The component may be present at an amount of at least 0.001 wt %, at least 0.005 wt %, at least 0.01 wt %, at least 0.05 wt % or at least 0.1 wt %.

The preferences above may apply when the component has a relatively large molecular weight, such as greater than 2,000, such as 5,000 or more, such as 10,000 or more.

The amount of component within a metal-organic framework, such as a crystalline metal-organic framework, may be determined by thermogravimetric analysis (TGA). Such methods are described herein.

In one embodiment, the metal-organic framework is provided, such as provided for use in methods of treatment, in a solvent, such as dissolved or suspended in water.

One or more solvents may be present. For example, water may be provided together with a solvent. A solvent may be a pharmaceutically acceptable solvent.

The metal-organic framework, holding the component, may be provided in a solvent in an amount of at most 1 wt %, at most 5 wt %, at most 10 wt % or at most 20 wt %.

The metal-organic framework, holding the component, may be provided in a solvent in an amount of at least 0.01 wt %, at least 0.05 wt %, at least 0.1 wt % or at least 0.5 wt %.

It is noted that the amorphous metal-organic framework described by Bennett et al. are apparently provided in the solid state.

Metal-organic frameworks are known to degrade under physiological conditions ("bioerosion"), thereby allowing release of a component held within the framework. As such, metal-organic frameworks are especially useful for releasing a component in vivo, for example within a method of treatment. As noted above, the principal components of the framework—the metal and the organic ligand—may have very low toxicity.

Component

The amorphous metal-organic framework holds a component. The component is releasable from the framework. The component is generally a useful compound whose encapsulation and subsequent release is desirable or beneficial. The amorphous metal-organic framework may be used as a delivery system, allowing the component to be held and delivered to a target location for release as required.

The present inventors have found that an amorphous metal-organic framework permits the sustained release of the component over an extended period of time. The use of an amorphous metal-organic framework avoids the problem associated with the crystalline form of the framework, which is shown to release a component rapidly and in an uncontrolled fashion.

In one embodiment, the component is an active agent for use in methods of medical treatment. For example, the component is an active agent for use in methods of treating a proliferative disease, such as cancer, such as cervical cancer.

In one embodiment, the component is an active agent for use in methods of treating a plant or a plant material, such as a flower, seed, fruit or tuber. Such methods are typically for the protection of the plant or plant material and/or to promote plant development.

In one embodiment, the component is a dye, such as a fluorescent dye. In one embodiment, the component is an agrochemical, for example a pesticide, such as an herbicide, insecticide, or fungicide.

In one embodiment, the component is or comprises a polypeptide, polynucleotide (including DNA- or RNA-based sequences) or a polysaccharide. For example, the component may be a polynucleotide, such as DNA- or RNA-based sequences, such as siRNA.

In one embodiment, the component is a compound, or a salt thereof, having a molecular weight that is at least 100, at least 125, at least 150, at least 200, at least 255, at least 300, or at least 500 g/mol.

In one embodiment, the component is a compound, or a salt thereof, having a molecular weight that is at most 1,000, at most 2,000, at most 5,000 or at most 10,000 g/mol. In one embodiment, the component is a compound, or a salt of a compound, having a molecular weight in a range having the upper and lower limits selected from the values given above. For example, the component is a compound, or a salt of a compound, having a molecular weight in the range 125 to 2,000, such as 255 to 2,000 g/mol.

Molecular weight may refer to weight average or number average molecular weight.

In one embodiment, the component has at least 3 atoms, at least 10 atoms or at least 20 atoms.

In one embodiment, the component has at most 50 atoms, at most 60 atoms, at most 70 atoms, at most 100 atoms, at most 200 atoms, at most 500 atoms, at most 1,000 atoms, at most 2,000 atoms or at most 10,000 atoms.

In one embodiment, the component has an atom number in a range having the upper and lower limits selected from the values given above. For example, the component has an atom number in the range 20 to 100 atoms, such as 20 to 70 atoms.

In one embodiment, a reference to a component is not a reference to a solvent molecule. For example, the component is not methanol and it is not ethanol.

In one embodiment, the component has a boiling point that is 80° C. or more, such as 90° C. or more, such as 100° C. or more.

In one embodiment, the component has a melting point that is 50° C. or more, such as 100° C. or more, such as 150° C. or more, such as 200° C. or more.

In one embodiment, the component has decomposes at a temperature of 50° C. or more, such as 100° C. or more, such as 150° C. or more, such as 200° C. or more.

The component is typically of a size that is able to enter into the pores of the crystalline metal-organic framework through the gates in the framework. It follows that the average largest cross section of the component is less than the average largest cross section of the gate. For example, the average largest cross section of the component is less than 3, less than 4, less than 5, less than 6, less than 7, or less than 8 Å. The size of a component may be known or may be determined by standard sizing techniques, such as dynamic light scattering. The size of a component may also be calculated from computational modelling of the metal-organic framework.

In one embodiment, the component is an organic compound, or a salt thereof. Thus, the component has one or more, such as two or more, carbon atoms, optionally together with one or more nitrogen, oxygen and/or sulfur atoms.

In one embodiment, the component has three or more carbon atoms.

In one embodiment, the component has one or more aromatic groups, such as a carboaromatic or heteroaromatic group. Many biologically active agents possess aromatic functionality, and the work in the present case shows that an aromatic-containing compound may be released from an amorphous metal-organic framework in a sustained manner.

In one embodiment, the component does not contain an iodine atom.

In one embodiment, the component is not molecular iodine ($I_2$).

In one embodiment, the component is a solid or a liquid under ambient conditions, such as a solid. Ambient conditions may refer to a temperature of 25° C. at a pressure of 101.3 kPa. The amorphous metal-organic framework is particularly suitable for holding and releasing non-volatile components.

In one embodiment, the component is hydrophilic. The present inventors have found that an amorphous metal-organic framework may be used to transport a hydrophilic component across a cell membrane, thereby to provide the component within the intracellular space. The hydrophilic component may be released from the framework as required into the intracellular space.

In one embodiment, the component has a partition coefficient, log P, not greater than 5, for example not greater than 4, for example not greater than 3.

In an alternative embodiment, the component is hydrophilic. Such compounds are also deliverable into the intracellular space.

In one embodiment, the component has a partition coefficient, log P, of more than 5, for example 6 or more, such as 7 or more.

The partition coefficient for a component may be determined experimentally from the partition of the component between water and 1-octanol, as measured at ambient temperature, such as 20 or 25° C. Alternatively, the partition coefficient of the component may be predicted using a standard quantitative structure-property relationship (QSPR) algorithm.

The worked example in the present case show that calcein may be released from an amorphous metal-organic framework in a delayed and controlled manner. The anticancer compounds dichloroacetate (DCA), α-Cyano-4-hydroxycinnamic acid (α-CHC) and 5-fluorouracil (5-FU) may also be released from an amorphous metal-organic framework in a delayed and controlled manner.

Methods of Preparing an Amorphous Metal-Organic Framework

An amorphous metal-organic framework may be prepared from a crystalline metal-organic framework. Methods for the amorphization of crystalline metal-organic frameworks are well known in the art.

The amorphization process is intended to destroy the long range order that is present within the crystalline metal-organic framework. The amorphous metal-organic framework has a highly disordered framework structure and lacks long range order. However, the amorphous framework retains basic metal-ligand connectivity that is also present in crystalline metal-organic framework. The amorphization process may be said to result in the structural collapse of the crystalline metal-organic framework.

The change in the metal-organic framework from a crystalline to an amorphous structure may be established by X-ray diffraction methods, and powder X-ray diffraction methods in particular. Typically the crystalline metal-organic framework possesses distinct Bragg reflections in the PXRD pattern. In the PXRD pattern for the metal-organic framework these Bragg reflections are lost. This is demonstrated in the present case for the amorphous and crystalline forms of UiO-66 holding calcein (see FIG. 1).

In the method of the invention, a crystalline metal-organic framework holding a component is subjected to amorphization, thereby to provide an amorphous metal-organic framework holding the component.

It is believed that the amorphization process causes the component to become entrapped in the porosity of the framework. The amorphization process brings about a collapse of the framework, which believed to be linked to the destruction of the metal-ligand groups in the framework.

In one embodiment, the amorphization is achieved by ball milling the crystalline metal-organic framework.

In another embodiment, the amorphization is achieved by heating the crystalline metal-organic framework, for example to a temperature of 100° C. or more, such as 200° C. or more, such as 300° C. or more. The heating temperature may be at most 400° C.

The heating temperature may be in the range 100 to 300° C., such as 100 to 200° C.

The framework may be heated for at 1 hour or more, such as 2 hours or more, such as 4 hours or more, such as 12 hours or more, such as 24 hours or more.

The framework may be heated under a reduced pressure: that is less than atmospheric pressure.

The heat treatment of the crystalline metal-organic framework may also result in the removal of solvent from the framework, as described below.

In another embodiment, the amorphization is achieved by the application of an electrical discharge to the crystalline metal-organic framework. This method is less preferred, as the methods of electrical treatment can lead to the decomposition of the organic ligands within the framework (as shown by Zhuo et al.). Thus, in one embodiment, the amorphization method is not an electrical discharge method, for example is not a dielectric-barrier discharge (DBD) method.

In a further embodiment, the amorphization is achieved by the application of a pressurizing force to the crystalline metal-organic framework, for example applying a pressure of at least 0.1, at least 1, at least 5 or at least 10 MPa. Here, a sample may be compressed in a hydraulic press.

In another embodiment, the amorphization is achieved by removal of a solvent from the crystalline metal-organic framework. The solvent may be removed by heating, such as at the temperatures described above, and/or at reduced pressure. In one embodiment, the solvent has a high surface tension, for example water. The removal of solvent from the porosity of the framework, such as at elevated temperatures, is believed to provoke the collapse of the framework porosity by the action of the internal forces in the liquid-gas meniscus. As a result, the component is entrapped within an amorphous metal-organic framework.

In one embodiment, the solvent has a surface tension, y, at 25° C. of at least 40, at least 50, at least 60 or at least 70 dyn/cm (mN/m). For example, water has a surface tension of 71.97 dyn/cm at 25° C.

In some embodiments, the amorphization may comprise one or more of the steps described above.

In other embodiments, the amorphous metal-organic framework may be prepared directly from the constituent components, and without the need to proceed via a crystalline metal-organic framework intermediate.

In one embodiment, the amorphous metal-organic framework holding the component is obtained or is obtainable from the crystalline metal-organic framework holding the component by ball milling.

A ball mill may be used to mill the crystalline metal-organic framework.

Ball milling may be performed with an appropriate ball size at an appropriate oscillation rate for an appropriate time to achieve the amorphization of a crystalline metal-organic framework.

The diameter of the ball (or balls) selected for use may be at least 1 mm, at least 2 mm, at least 4 mm or at least 5 mm.

The diameter of the ball (or balls) selected for use may be at most 10 mm, at most 15 mm or at most 20 mm.

The ball milling process may use an 8 mm ball. The ball milling process may use a 7 mm ball. The size of the ball may be varied in order, for example, to vary the size of the particles in the amorphous metal-organic framework.

The ball is typically of a density and/or harness greater than the density of the crystalline metal-organic framework. In one embodiment, the ball is a steel ball, such as a stainless steel ball.

The oscillation frequency of the ball milling may be at least 1 Hz, at least 5 Hz, at least 10 Hz, or at least 15 Hz.

The oscillation frequency of the ball milling may be at most 25 Hz, at most 50 Hz, or at most 100 Hz.

Typically, ball milling is performed at an oscillation rate of around 20 Hz.

The ball milling may be performed for at least 10 minutes, at least 20 minutes or at least 30 minutes. Alternatively, ball milling may be performed for at least 1 minute, at least 2 minutes or at least 5 minutes.

The ball milling may be performed for at most, 40 minutes, at most 60 minutes, at most 90 minutes or at most 120 minutes.

It may be beneficial to avoid extensive ball milling times in order to avoid overly collapsing the internal void volume of the amorphous metal-organic framework. It is also necessary to mill the crystalline metal-organic framework for a sufficient time to ensure that the component is entrapped, thereby ensuring that the component can be released over a sustained period of time.

Typically, the ball milling is performed for around 30 minutes.

The ball milling amorphization process does not apparently degrade the component held within the framework.

A crystalline metal-organic framework holding a component may be obtained or is obtainable from a crystalline metal-organic framework by addition of the component thereto.

In one embodiment, the method of preparing an amorphous metal-organic framework holding the component comprises the preliminary step of preparing a crystalline metal-organic framework holding the component.

The crystalline metal-organic framework may be mixed together with the component, optionally within a solvent and optionally at elevated temperature, such as a temperature greater than the ambient temperature, for example at 20° C. or more, such as 25° C. or more, such as 30° C. or more.

Pharmaceutical Composition

The present invention provides a pharmaceutical composition comprising an amorphous metal-organic framework holding a component. Here the component is an active agent for use in methods of medical treatment. The amorphous metal-organic framework is optionally provided together with one or more pharmaceutically acceptable ingredients.

The pharmaceutical composition finds use in methods of medical treatment, as discussed in further detail below.

The amorphous metal-organic framework may be formulated together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilizers, solubilisers, surfactants (e.g., wetting agents), masking agents, colouring agents, flavouring agents, and sweetening agents. The formulation may further comprise other active agents, for example, other therapeutic or prophylactic agents. Thus, the present invention further provides pharmaceutical compositions, as defined above, and methods of making a pharmaceutical composition comprising admixing an amorphous metal-organic framework, as defined above, together with one or more other pharmaceutically acceptable ingredients well known to those skilled in the art, e.g., carriers, adjuvants, excipients, etc. If formulated as discrete units (e.g., tablets, etc.), each unit contains a predetermined amount (dosage) of the active compound.

The term "pharmaceutically acceptable" as used herein pertains to ingredients, materials, compositions, dosage forms, etc., which are, within the scope of sound medical judgement, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. For example, the composition may be formulated for administration via the oral route as an aerosol, as is well known in the art, such as for the administration of active agents for the treatment of asthma.

Further teaching regarding suitable carriers, adjuvants, excipients, etc. can be found in standard pharmaceutical texts, for example, Remington: The Science and Practice of Pharmacy", $20^{th}$ Edition, 2000, pub. Lippincott, Williams & Wilkins; and Handbook of Pharmaceutical Excipients, $2^{nd}$ edition, 1994.

Release of the Component

The present invention provides a method for releasing a component from the amorphous metal-organic framework. The present inventors have found that the component release is controlled, sustained and relatively slow, for example as compared with the release of a component from a crystalline metal-organic framework.

Such a release has use in methods of treatment where it is desirable to have sustained release of an active agent over a significant time period, for examples over 5, 10 or 15 days. This is described in further detail below.

In one embodiment, the component is released from the complex into an aqueous phase. Thus, the amorphous metal-organic framework may itself be provided in an aqueous mixture for the release of the component into the aqueous phase. Here, the aqueous phase may include an aqueous environment within a cell, and/or an aqueous environment in vivo. The inventors have shown in this work that an organic dye is releasable from a zirconium-based framework into a HeLa cell.

In one embodiment, the component is releasable from the amorphous framework upon treatment of the amorphous framework with base or acid, such as aqueous base or aqueous acid.

In one embodiment, the component is releasable from the amorphous framework upon treatment of the amorphous framework with an aqueous mixture having a physiological pH, such as pH of about 7.4.

In other embodiments, the component is releasable from the amorphous framework upon heating, for example at a temperature of at least 50° C., at least 100° C. or at least 200° C.

In yet a further embodiment, the component is releasable from the amorphous framework under reduced pressure, including the release of the component upon heating and at reduced pressure (for example, within a vacuum oven). Reduced pressure is a pressure that is less than ambient pressure, for example at a pressure of less than 101.3 kPa, such as a pressure of less than 90 kPa.

The release of a component from an amorphous metal-organic framework is delayed compared with the release of the component from the corresponding crystalline metal-organic framework, for example the crystalline metal-organic framework from which the amorphous form is obtained.

In the methods of the invention, including the methods of treatment, the component is released from the framework over a sustained period of time. The inventors have found that the use of crystalline frameworks can be associated with relatively rapid release of the component from the framework. By amorphization of the crystalline metal-organic framework it is possible to entrap a component within the framework. The relatively rapid release of the component from the framework is therefore prevented or minimised. Thus, in the worked examples, it is shown that a burst release of component from a crystalline metal-organic framework is prevented in an amorphous metal-organic framework. Furthermore, the use of a metal-organic framework anyway provides for delayed release compared with the use of the component in free form.

In one embodiment, the amorphous metal-organic framework releases less of the held component compared with the corresponding crystalline form of that framework, for example as determined at 12 hours, 24 hours, 48 hours, or more, such as after 3 days, 7 days, 14 days or 28 days, from initial release.

In some embodiments, the release of a component from an amorphous metal-organic framework and the crystalline forms of the amorphous metal-organic framework is at substantially the same rate, and this rate may be a delayed release. The amorphous form may therefore be a suitable replacement for the crystalline form in a component delivery system. The use of amorphous metal-organic framework for delivery is therefore an alternative to the crystalline delivery systems described by, for example, He et al. (*J. Am. Chem. Soc.*, 2014, 136, 5181).

In the present case, it is shown that the crystalline version of UiO-66 releases substantially all of a held component over a period of 12 hours. In contrast, when the component is held in an amorphous version of UiO-66, substantially all of the component is released over a period of more than 30 days.

In one embodiment, an amorphous metal-organic framework holding a component releases no more than 50% of the component after 12 hours, 24 hours, 48 hours, or more, such as after 3 days, 7 days, 14 days or 28 days.

In one embodiment, an amorphous metal-organic framework holding a component releases no more than 70% of the component, after 48 hours, or more, such as after 3 days, 7 days, 14 days or 28 days.

In one embodiment, an amorphous metal-organic framework holding a component releases 50% of the component over a period of time that is a least 1 hour, at least 2 hours, at least 4 hours, at least 12 hours, at least 24 hours or at least 48 hours longer than the release of 50% of the component from the corresponding crystalline metal-organic framework.

In one embodiment, an amorphous metal-organic framework holding a component releases 70% of the component in at least 1 hour, at least 2 hours, at least 4 hours, at least 12 hours, at least 24 hours, at least 48 hours, at least 3 days, at least 7 days or at least 28 days longer than the release of 50% of the component from the corresponding crystalline metal-organic framework.

The release kinetics of the amorphous metal-organic framework holding the component may be compared with the crystalline metal-organic framework holding the component from which it is obtained.

The release period is determined with respect to the initial release of component from the framework.

The amount of component released is quoted with respect to the total amount of component held in the framework prior to release (which may be known from the methods of preparation). The amount of component released may be determined by standard spectroscopic techniques. In the worked examples, the absorbance characteristics of the released component is used to gauge the quantity of material released. Percentage amounts of component released may refer to mole % or wt % of the total amount of component held in the framework.

In one embodiment, the amorphous metal-organic framework allows continuous release of a component over a period of at least 2 days, at least 3 days, at least 7 days, at least 10 days, at least 14 days, or at least 28 days. The continuous release is not necessarily a constant rate of release. Indeed, as discussed below, the rate of release may change over time.

The amorphous metal-organic framework may allow substantially all of a held component to be released from the framework. Thus, in one embodiment, at least 80%, such as at least 90%, such as at least 95%, of the component is released or is releasable from the amorphous metal-organic framework.

In an alternative embodiment, the amount of component released from the amorphous metal-organic framework is at least 20%, at least 25%, at least 50% or at least 60%.

The amount of component released from the metal organic framework may be determined at 5 days, 10 days, 14 days, 28 days or 50 days. In an alternative embodiment, the amount of component released from the metal organic framework may be determined at 2 or 3 days. In one embodiment, at least 80% of the component is released after 28 days.

It has been found that an amorphous metal-organic framework may release a component in two stages. There may be an initial, relatively rapid release phase of a part of the component.

This release is associated with desorption and diffusion along the amorphous pore texture of the framework. The second release phase is a relatively slow release. This release is associated with the partial dissolution of defects in the porous structure thereby to liberate remaining encapsulated component. Substantially all remaining component is released in this second phase. The second phase a substantially linear release profile.

Typically, no more than 10%, nor more than 20%, no more than 30, no more than 40%, no more than 50%, or no more than 50% of the component is released in the initial release. The initial release may be an initial release period of at most 4 hours, at most 12 hours, at most 24 hours or at most 48 hours.

Methods of Treatment

In one aspect of the invention there is provided an amorphous metal-organic framework for use in a method of treatment, wherein the amorphous metal-organic framework holds a component, and the component is an active agent for use in methods of medical treatment. Similarly, the pharmaceutical composition of the invention is also provided for use in a method of treatment.

In the methods of treatment it is not intended that the amorphous metal-organic framework itself should be used as an active agent for medical treatment. Rather, it is the component held within the framework that has the relevant biological activity. Thus, the amorphous metal-organic framework is a carrier for the biologically-active component, and is intended to protect and deliver the component to a target location.

The amorphous metal-organic framework is capable of crossing the cell membrane of eukaryotic cells. Thus, the amorphous metal-organic framework is suitable for delivering a component into a cell and releasing a component within that cell.

As noted above, an amorphous metal-organic framework allows release of a held component in a controlled and sustained manner. The amorphous metal-organic framework is therefore suitable for use in methods of treatment where it is clinically beneficial to release an active agent over a sustained period of time.

Here the component is an active agent that is suitable for use in a method of treatment. The component is formulated within the amorphous metal-organic framework, and the amorphous metal-organic framework is used to deliver the active agent to a suitable location within the subject o be treated. The component is releasable from the amorphous metal-organic framework.

In an alternative aspect there is provided an active agent for use in methods of medical treatment, wherein the active agent is held within an amorphous metal-organic framework. In one embodiment, the amorphous metal-organic framework is provided within a pharmaceutical composition.

In the methods of treatment the component is released from the amorphous metal-organic framework, thereby to be made available. As discussed above, the amorphous metal-organic framework is suitable for releasing a component over an extended period.

In one embodiment of the invention the amorphous metal-organic framework holding the component is for treatment of a proliferative disease, such as cancer. Thus, the component is an active agent for the treatment of a proliferative disease, such as cancer. The cancer may be cervical cancer. The worked examples provided herein show that a metal-organic framework is deliverable into a HeLa cell or a HEK-293 cell line.

Methods of Delivery

In a further aspect of the invention there is provided the use of an amorphous metal-organic framework to deliver a component to a target location. The component is held by the metal-organic framework, and the component may be released from the framework once the metal-organic framework is provided at the target location.

Thus, in one aspect of the invention there is provided a method of delivering a component to a target location, the method comprising the steps of:
(i) providing an amorphous metal-organic framework at a target location, wherein the amorphous metal-organic framework holds a component; and
(ii) permitting the release of the component from the amorphous metal-organic framework, thereby to provide the component at the target location.

In one embodiment, the target location is within a cell (intracellular), such as a proliferative cell, such as a cancer cell.

In one embodiment, the target location, such as a cell, is in vivo.

In one embodiment, the target location, such as a cell, is ex vivo.

In one embodiment, the target location is an extracellular location.

In one embodiment, the step of providing the amorphous metal-organic framework at the target location includes passing the amorphous metal-organic framework thorough a cell membrane. The cell membrane may the membrane of a proliferative cell, such as a cancer cell. The cell membrane may be eukaryotic or prokaryotic cell membrane.

In one embodiment, the step of providing the amorphous metal-organic framework at the target location includes the step of passing the amorphous metal-organic framework along a capillary, such as a microcapillary.

In the delivery method the amorphous metal-organic framework may be formulated in a pharmaceutical composition suitable for delivery to the target location.

The release of the component may be achieved by exposure of the amorphous metal-organic framework to base, such as aqueous base. The component may be released under physiological conditions, such as at pH 7.4.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental

Instrumentation

The PXRD data were collected in Bragg-Brentano geometry on a D8 Bruker diffractometer equipped with a primary Ge monochromator for Cu K$\alpha$1 and a Sol-X solid state detector. Collection conditions were: 2-70° in 2$\theta$, 0.02° step size, 15 seconds/step, divergence slits 0.2 mm, receiving slit 0.2 mm.

Samples for SEM were scattered onto spectroscopically-pure carbon tabs (TAAB Ltd UK) mounted on aluminium stubs. The samples were coated with 15 nm of gold in a Quorum Emitech K575X sputter coater to make them electrically conductive. The samples were imaged in an FEI XL30 FEGSEM, operated at 5 keV, using an Everhart Thornley secondary electron detector.

Thermogravimetric analysis (TGA) was performed using a TA Instruments Q-500 series thermal gravimetric analyser, with the sample (0.7-5 mg) held on a platinum pan under a continuous flow of dry $N_2$ gas. TGA curves were obtained using a heating rate of 5° C./min up to 600° C.

$N_2$ adsorption isotherms were undertaken at 77 K using a Micromeritics TriStar instrument.

Synthesis and Characterization

The zirconium-based MOF UiO-66 (UiO=University of Oslo) $[Zr_6O_4(OH)_4(BDC)_6]$ (BDC=1,4-benzenedicarboxylate) was used as an exemplary metal-organic framework for delivery of a component to a target location.

UiO-66 has a cubic structure based on Zr oxo-clusters and BDC ligands (see Cavka et al.), and possesses high thermal and chemical stability combined with a large porosity (SBET 1200 $m^2$ $g^{-1}$, Vp~0.5 $cm^3$ $g^{-1}$) formed by two main cavities (Øcavity~11 and 8 A; Øgate~5 and 7 Å) (see Cunha et al.). Additionally, Zr has low toxicity (zirconyl acetate lethal dose $LD_{50}$~4.1 mg/mL in rats; furthermore, the human body contains ~300 mg of Zr and the amount daily ingested is ~3.5 mg/day).

Crystalline UiO-66 was obtained following the procedure described by Katz et al. Thus, $ZrCl_4$ (0.125 g) was dissolved in a mixture of DMF (5 mL) and HCl (1 mL, 37%). Separately, terephthalic acid (BDC, 0.123 g) was dissolved in DMF (10 mL). The two solutions were mixed in a 25 mL teflon-lined autoclave and heated at 80° C. for 16 hours. The resulting solid was collected by centrifugation at 5,500 rpm for 10 minutes, and then washed with DMF and ethanol three times. The white product was then dried at 90° C. in a vacuum oven in order to remove remaining solvent.

Figure 5:
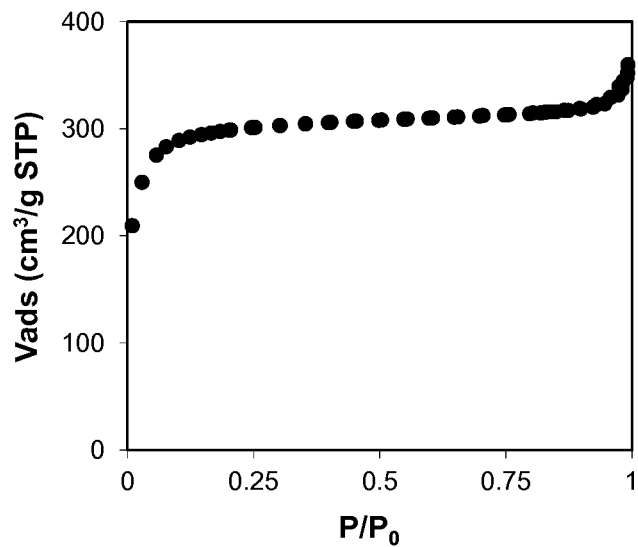
FIG. 5 is the $N_2$ adsorption isotherm at 77 K for crystalline UiO-66.
Figure 6:
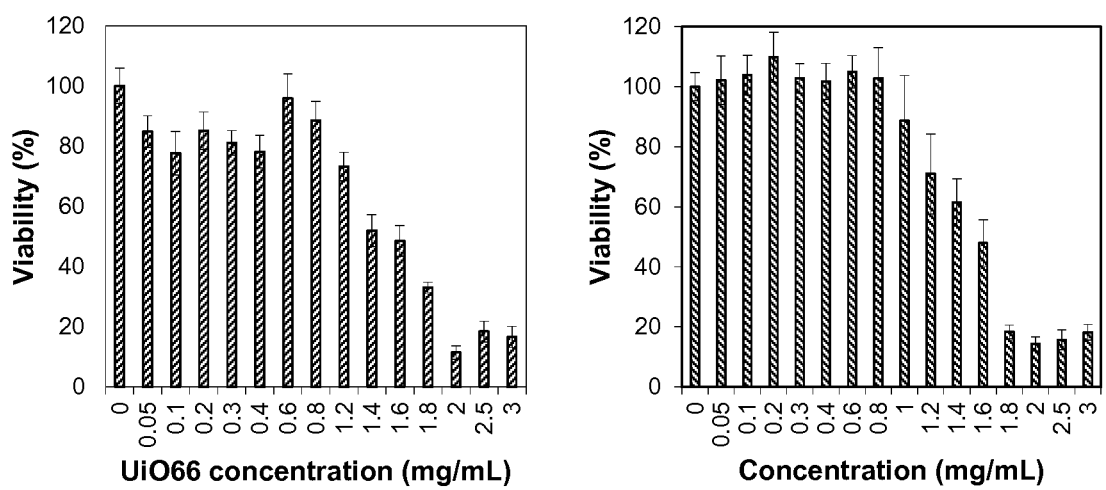
FIG. 6 shows the change in HELA cell viability (%) with the change in crystalline UiO-66 concentration (mg/mL).

The porosity of crystalline UiO-66 was analyzed using $N_2$ adsorption at 77 K (see FIG. 5). Prior to the analysis, 100 mg of the sample were evacuated for 24 h at 150° C. under vacuum. The BET area of synthesized UiO-66 was 1,166 $m^2$/g: similar to the values previously reported in the literature (see Cavka et al. and Cunha et al.).

Loading Experiments

Calcein was selected as a model active agent in view of its hydrophilic nature, which renders the compound impermeable to cell membranes. In addition, being a fluorescent molecule, calcein can be easily traced by confocal microscopy. Due to its self-quenching characteristics, high local concentrations of calcein (e.g. when it is adsorbed in into a metal-organic framework) cannot be detected. Accordingly, when calcein is detected it is generally associated with the release of the agent from the framework.

Calcein adsorption was performed by soaking crystalline UiO-66 (20 mg) into 5 mL of methanol calcein solution (5 mg/mL) at 37° C. under orbital agitation for 6 days. The loaded material was obtained after centrifugation at 5,500 rpm for 20 minutes, washed twice with methanol, centrifuged again for 10 minutes and dried overnight at 37° C. to remove the solvent.

The amount of calcein adsorbed was quantified using a UV-vis spectrophotometer at 498 nm, measuring the amount of drug present in the supernatant after the first centrifugation step.

The loaded amount is given by the equation [1]:

$$\text{Loading (wt. \%)} = \frac{calcein_{added} \text{ (mg)}}{calcein_{added} \text{ (mg)} + \text{material (mg)}} \quad [1]$$

where calceinadded is the amount of calcein at t=0, and material is the amount of crystalline UiO-66 added.

MOF Amorphization

Calcein-loaded crystalline UiO-66 (cal@UiO-66, 0.2 g) was placed in a stainless steel jar along with an 8 mm stainless steel ball. The jar was then oscillated at 20 Hz for 30 minutes using a Retsch MM200 mill resulting in amorphous calcein-loaded UiO-66 (cal@aUiO-66).

PXRD, SEM and TGA Analysis

Crystalline UiO-66, calcein-loaded crystalline UiO-66 (cal@UiO-66) and calcein-loaded amorphous UiO-66 (cal@aUiO-66) were analyzed by powder X-ray diffraction (PXRD).

Comparison of the calculated diffraction pattern for crystalline UiO-66 with cal@UiO-66 confirmed structural retention (see FIG. 1). Ball-milling amorphization of cal@UiO-66 to produce cal@aUiO-66 resulted in the loss of long range order and associated Bragg reflections from the PXRD pattern of the amorphous material.

Figure 4:
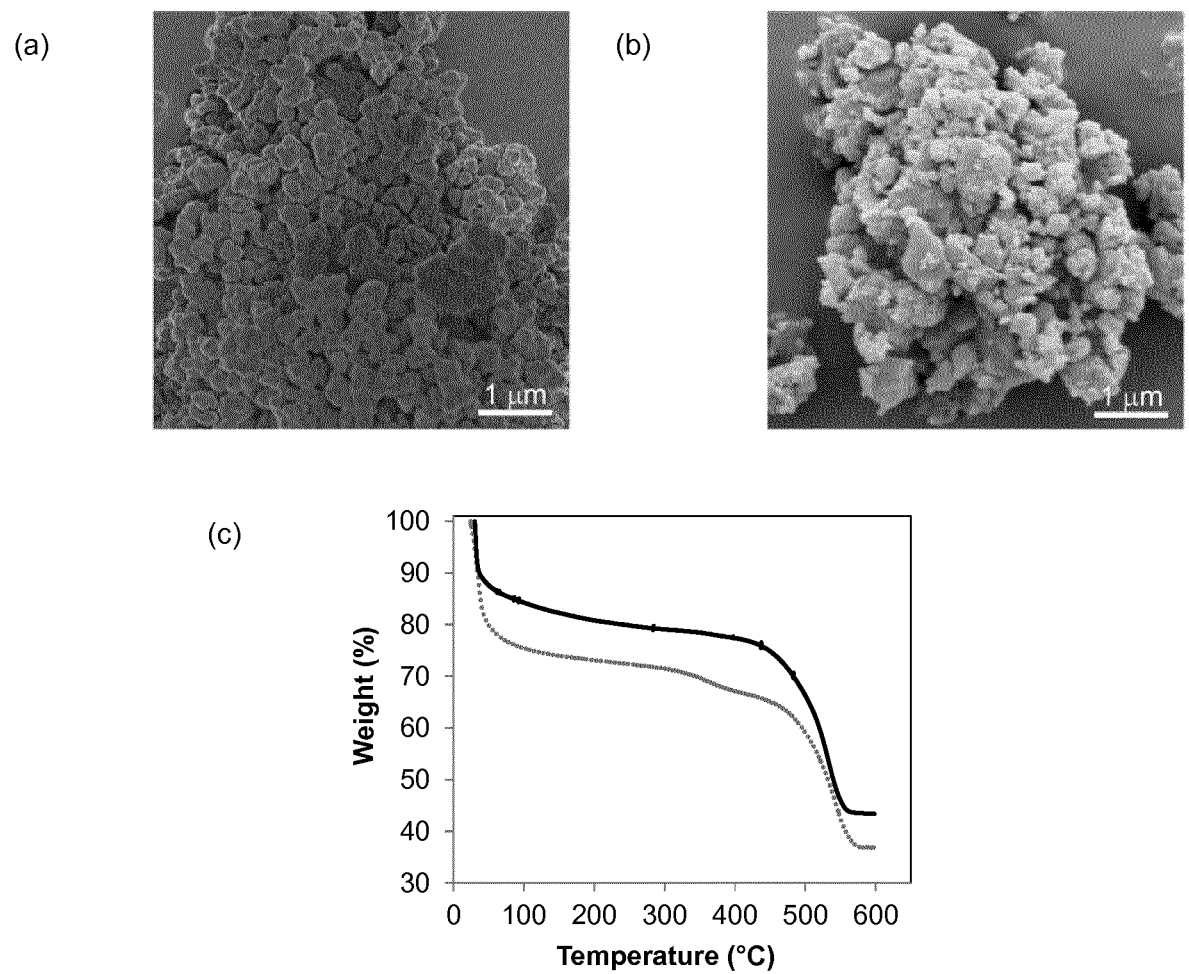
FIG. 4 includes an SEM image (a) of crystalline UiO-66 (UiO-66) and (b) amorphous UiO-66 (aUiO-66), where the scale bar is 1 µm; and (c) a TGA curve showing the change in weight (%) with change in temperature (° C.) for crystalline UiO-66 (UiO-66, continuous line) and crystalline UiO-66 holding calcein (cal@UiO-66, dashed line).

The scanning electron microscopy (SEM) images of crystalline UiO-66, revealed a particle size of 261±12 nm (see FIG. 4). The morphology of the particles after amorphization is less homogeneous, with a particle size of 272±157 nm.

The thermogravimetric analysis (TGA) of crystalline UiO-66 revealed a first weight lost below 100° C., which corresponds to the desorption of solvent molecules, followed by the solid degradation at ca. 475° C. (see FIG. 4c). The thermogravimetric analysis of cal@UiO-66 shows an additional step at ca. 400° C., which corresponds to the calcein desorption from the material. The amount of calcein loaded, measured by TGA, was 4.9±0.2 wt %.

The size of calcein molecule and the pore gate diameter of the material restrict the possibility of a larger loaded amount. Nevertheless, this amount is sufficient for use in methods of controlled delivery from an amorphous material.

Delivery Assays

Calcein release experiments were performed in an incubator at 37° C. with orbital agitation and using phosphate buffered saline (PBS, 10 mM) at pH 7.4 in order to simulate physiological conditions. Calcein-loaded amorphous and crystalline UiO-66 (3 mg) was placed into a dialysis bag (MWCO 3,500, molecular weight cut-off Da, Medicell International) with a total volume of 10 mL of PBS. At different times, 1 mL of PBS was taken and replaced with 1 mL of fresh PBS. The amount of drug released was measured using a UV-vis spectrophotometer at 498 nm. The corrected concentration of calcein release is given by the equation [2]:

$$c_t = c'_t + \frac{v}{V} \sum_{0}^{t-1} c'_t \quad [2]$$

where $c_t$ is the corrected calcein concentration at time t, $c'_t$ is the apparent calcein concentration, v is the sample taken and V is the total volume of the solution. Every experiment was performed in triplicate.

The kinetics of calcein delivery from crystalline and amorphous UiO-66 were adjusted using non-linear regressions in order to understand the release behaviour. For the crystalline material the delivery was adjusted to a simple hyperbola model [3]:

$$N \text{ (wt. \%)} = \frac{N_{max} t}{(t_{1/2} + t)} \quad [3]$$

where N is the amount released from the total drug-loaded amount in weight percent, $N_{max}$ is the maximum amount released, t is time in days and $t_{1/2}$ is the time needed to get half of the maximum amount delivered.

For amorphous calcein-loaded UiO-66 (cal@aUiO-66) it was not possible to adjust the delivery to a simple curve. In this case, a hyperbola model considering two different release stages was used [4]:

$$N \text{ (wt. \%)} = \frac{N_{max}(1) t}{(t_{1/2}(1) + t)} + \frac{N_{max}(2) t}{(t_{1/2}(2) + t)} \quad [4]$$

where $N_{max}$ and $t_{1/2}$ are considered for two stages: (1) and (2).

Figure 2:
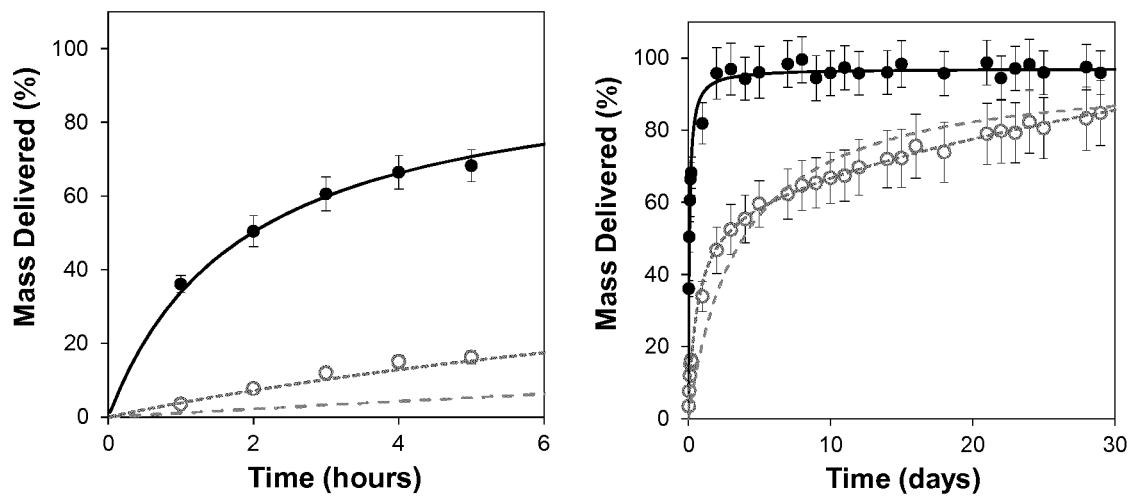
FIG. 2 shows the mass of calcein released over time (hours, left, and days, right) from amorphous UiO-66 (cal@aUiO-66, open circles) and crystalline UiO-66 (cal@UiO-66, filled circles). The black solid and red dotted lines represent the kinetic of delivery fitting using non-linear regression on cal@UiO-66 and cal@aUiO-66 respectively. Blue dashed line represents the fitting for cal@aUiO-66 using Eq [3]. The mass of calcein released is given as a percentage of total calcein deliverable from the amorphous or crystalline UiO-66.
Figure 3:
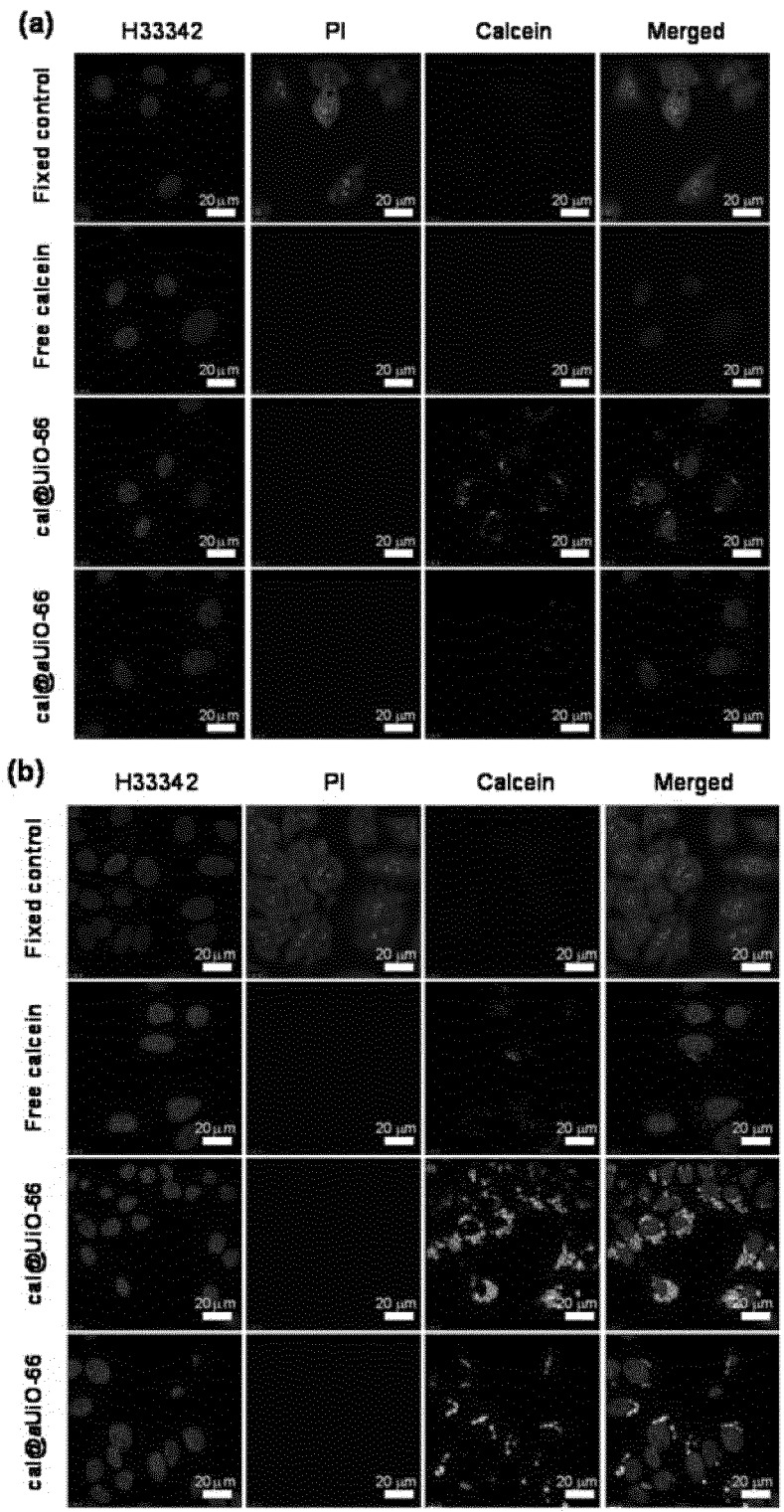
FIG. 3 is a series of confocal microscopy images of HeLa cells incubated for (a) 24 hours and (b) 48 hours. The cells were incubated with 4% PFA (fixed control, top row), free calcein (0.013 mg/mL, second from top), cal@UiO-66 (0.25 mg/mL, second from bottom) or cal@aUiO-66 (0.25 mg/mL, bottom), at 37° C. with 5% $CO_2$ in DMEM. Cells were subsequently stained with Hoechst 33342 (5 µg/mL) and PI (5 µg/mL).

FIG. 2 and Table 1 show the fitting of the experimental release and fitting parameters, respectively, for crystalline and amorphous calcein-loaded UiO-66.

The maximum amount of calcein delivered by cal@UiO-66 was 97.07 wt % and half of that amount was released within 1.86 h. The observed two-stage release pattern of cal@aUiO-66 is believed to be related to the existence of two different release phenomena. During the first phase, release of calcein is thought to proceed through desorption and diffusion along the amorphous pore texture of the material. About 58 wt % of the calcein is releasable this way, and half of this amount is released within 14 h indicating the much slower diffusion compared with cal@UiO-66.

The second release stage is a much slower process that is thought to be associated with the partial dissolution of defects of the aUiO-66, thereby to liberate the encapsulated calcein.

TABLE 1

Fit-curves for calcein release from crystalline and amorphous UiO-66.

| Material | Equation | $R^2$ |
|---|---|---|
| cal@UiO-66 | cal (wt %) = 97.07 t/(0.07762 + t) | 0.9908 |
| cal@aUiO-66 | cal (wt %) = 58.16 t/(0.6008 + t) + 97.07 t/(72.24 + t) | 0.9982 |

As it was possible to detect the calcein delivered form the amorphous material it was reasonable to conclude that the ball-milling process did not cause the degradation of the guest.

Cell Culture

HeLa cells were maintained at 37° C. with 5% $CO_2$ in high rich glucose (4,500 mg/L) Dulbecco's modified Eagle's Medium (DMEM) supplemented with 10% (v/v) Fetal Bovine Serum (FBS), 2 mM L-glutamine, 100 units/mL penicillin and 100 µg/mL streptomycin. The cells were passaged three times a week (at 75-80% of confluence) at a density of $2.8 \times 10^4$ cell/$cm^2$.

Cytotoxicity Assays

The cytotoxicity activity of empty crystalline UiO-66 was investigated using the 3-(4,5-dimethylthiazol-2-yl)-5-(3-carboxymethoxyphenyl)-2-(4-sulfophenyl)-2H-tetrazolium (MTS) (Promega, UK) reduction assay. The day before the experiment, HeLa cells were seeded into a 96 well plate at a density of $5 \times 10^3$ cells per well. Prior to treatment, the cells were washed twice with PBS.

The UiO-66 samples were dispersed in cell culture media containing 0.5% of DMSO at a range of concentrations. The culture media containing UiO-66 were then added to the cells and incubated for 24 and 48 h at 37° C. with 5% $CO_2$.

To measure toxicity, the cells were washed extensively to remove the solids, the media was replace with fresh culture media (100 µL) containing MTS/phenazine methosulfate solution (20 µL, in a proportion 20:1) and the plate was incubated for 1 h at 37° C. with 5% $CO_2$. The plates were visualized at 490 nm.

It was confirmed that the DMSO concentrations used in the experiments was not toxic to the HeLa cells.

The $IC_{50}$ values were measured at 24 and 48 h. The values found were 1.503±0.154 mg/mL and 1.357±0.088 mg/mL for 24 and 48 h respectively. These values are similar to the reported for MIL Fe-based MOFs (see Tamames-Tabar et al.).

Amorphous UiO-66 is expected to have the same toxicity profile as crystalline UiO-66: the toxicity results are related to the constituent components that are common to the amorphous and crystalline forms of the metal-organic framework.

Confocal Microscopy

For cell penetration assays, HeLa cells were seeded in a NUNC™ imaging four-well plate at a density of $1.11 \times 10^5$ cell/mL and incubated for 24 h at 37° C. with 5% $CO_2$ in DMEM. The cells were then washed twice with PBS and incubated with 0.25 mg/mL of either crystalline calcein-loaded UiO-66 (cal@UiO-66) or amorphous calcein-loaded UiO-66 (cal@aUiO-66) for 24 and 48 h. The loaded materials were well disperse in culture media before being added to the well plates containing the cells. Untreated cell and free calcein were included as controls (0.013 mg/mL). Hoechst 33342 (H33342) and propidium iodide (PI) (each at 5 µg/mL) were used for staining the nucleus and as a viability control respectively.

After the incubation time, cells were washed several times to remove all the non-internalized material. Untreated cells were fixed with 4% p-formaldehyde (PFA) for 5 min and later all the samples were incubated with media containing the dyes H333421 and PI for 15 min. The cells were then washed extensively to remove the dyes, and then fresh media (without phenol red) was added to each sample. Finally, the four-well plate was placed on a Leica TCS SP5 confocal microscope for imaging. The microscope was equipped with 405 diode, argon and HeNe lasers. Leica LAS AF software was used to analyse the images.

Additional Experimental Work

A series of further amorphous frameworks was prepared. These frameworks included an isoretricular Zr-based family of MOFs with each having a different dicarboxylate organic ligand. Six different ligands, L1 to L6, were used, and these are shown below:

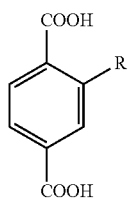

L1, R = ——H
L2, R = ——Br
L3, R = ——NO$_2$
L4, R = ——NH$_2$

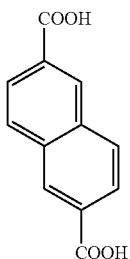

L5

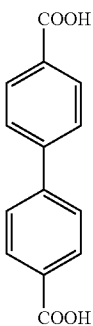

L6

The metal organic frameworks are referred to as Zr-L1 to Zr-L6 respectively.

Also prepared were Zr-containing NU-1000 and NU-901, and Bi-containing CAU-7. NU-901 includes the H$_4$TBAPy ligand shown, and CAU-7 includes the H$_3$BTB ligand, also shown below.

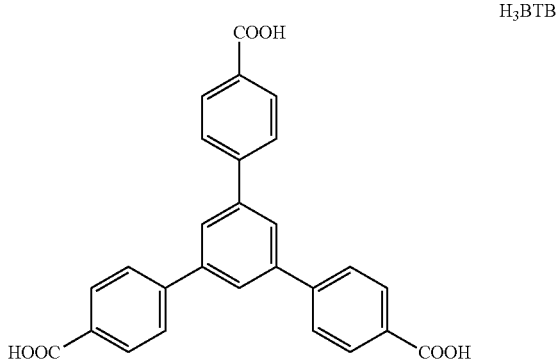

H$_3$BTB

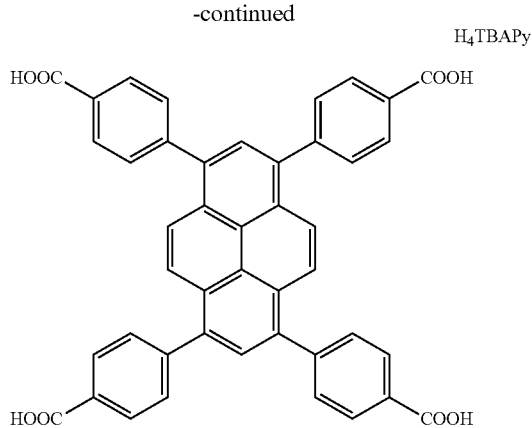

H$_4$TBAPy

The syntheses are described below. Zr-L1 corresponds to UiO-66, the preparation of which is described above.

Synthesis

Zr-L2 to Zr-L4 were synthesised by adding the required linker L2, L3 or L4 (2.70 mmol, 1 eq.) and ZrCl$_4$ (0.629 g, 2.70 mmol, 1 eq.) to 250 mL reagent bottles. DMF (60 mL) and hydrochloric acid (0.24 mL) were added and the mixture was sonicated for 10 minutes before the mixture was placed in the oven at 120° C. for 24 h. After this time the bottles were removed and allowed to cool to room temperature. The product was collected by centrifugation, washed with DMF (30 mL) and acetone (2×30 mL). The samples were placed in a vacuum desiccator to dry.

Zr-L5 and Zr-L6 were synthesised by adding L-proline (1.554 g, 13.50 mmol, 5 eq.), the required linker L5 or L6 (2.70 mmol, 1 eq.) and ZrCl$_4$ (0.629 g, 2.70 mmol, 1 eq) to 250 mL reagent bottles. DMF (60 mL) and hydrochloric acid (0.24 mL) were added and the mixture was sonicated for 10 minutes before the mixture was placed in the oven at 120° C. for 24 h. After this time the bottles were removed and allowed to cool to room temperature. The product was collected by centrifugation, washed with DMF (30 mL) and acetone (2×30 mL). The samples were placed in a vacuum desiccator to dry.

CAU-7 synthesis: 1,3,5-benzenetrisbenzoic acid (H$_3$BTB) (200 mg, 0.46 mmol) and Bi(NO$_3$)$_3$.5H$_2$O (148 mg, 0.31 mmol) were mixed in 30 mL microwave glass reaction vessels (Biotage) to which methanol (99.8%, 20 mL) was added. The reaction vessels were sealed with a septum, and the reaction mixture was homogenized and heated to 120° C. for 20 min in a Biotage Initiator microwave synthesizer. The mixture was stirred with a magnetic stirring bar during the reaction. The resulting yellow precipitate was filtered, washed with methanol, DMF and methanol again. The product was identified as pure CAU-7 by X-ray powder diffraction.

NU-1000 was prepared following the protocol of Mondloch et al. (*J. Am. Chem. Soc.* 2013, 135, 10294), which describes both the preparation of the H$_4$TBAPy ligand, and the preparation of NU-1000. ZrCl$_4$ (70 mg, 0.30 mmol) and benzoic acid (2,700 mg, 22 mmol) were mixed in DMF (8 mL) and ultrasonically dissolved. The clear solution was incubated in an oven at 800° C. for 1 h, and then allowed to cool to room temperature. H$_4$TBAPy (40 mg, 0.06 mmol) was then added to this solution; the mixture was sonicated for 20 min. The yellow suspension was heated in an oven at 1,200° C. for 48 h and then allowed to cool to room temperature. The resulting material was isolated by filtration (35 mg of activated material, 54% yield) and washed with DMF, and subsequently activated with HCl. The material is then heat treated at 70° C. in a vacuum oven overnight in order to remove any residue solvent left in the porosity.

NU-901 was prepared following the protocol of Kung et al. (*Chem. Mater.* 2013, 25, 5012), which describes both the preparation of the H$_4$TBAPy ligand, and the preparation of NU-901. ZrCl$_4$ (35 mg) and benzoic acid (1.35 g) were mixed in DMF (8 mL) and ultrasonically dissolved. The solution was incubated in an oven at 80° C. for 2 h, and then allowed to cool to room temperature. H$_4$TBAPy (20 mg) was added to this solution and the mixture was sonicated for 20 min. The resulting yellow suspension was heated in an oven at 120° C. for 4.5 h, and then allowed to cool to room temperature. Precipitated material was removed and the sample was washed with DMF. The material is then heat treated at 70° C. in a vacuum overnight in order to remove any residue solvent left in the porosity.

NU-1000 and NU-901 are based on a core octahedral Zr$_6$ cluster. NU-901 has pores of diagonal or rhombus shape, whilst NU-1000 has mostly hexagonal pores with some small triangular pores. The differences in geometry are achieved through the differences in the synthesis methods.

Loading Experiments

The metal-organic frameworks prepared in the experiments above were then loaded with calcein, an anticancer drug or siRNA. The model components for loading into the frameworks were calcein, and one of three anti-cancer drugs selected from dichloroacetate (DCA), α-Cyano-4-hydroxycinnamic acid (α-CHC) and 5-fluorouracil (5-FU).

The calcein adsorption was performed by soaking the metal-organic framework (Zr-L1 to Zr-L6; 100 mg) in a methanol calcein solution (25 mL; 5 mg/mL) at 37° C. under orbital agitation for 6 days. The calcein adsorption for NU-1000 was performed by soaking 10 mg of the metal-organic framework into 5 mL of aqueous calcein solution (10 mg/mL in deionized water, pH adjusted to ~7.5) at 37° C. under orbital agitation for 3 days.

The calcein adsorption for NU-901 was performed by soaking the metal-organic framework (100 mg) into deionized water calcein solution (50 mL; 10 mg/mL, pH adjusted to ~7.5) at 37° C. under orbital agitation for 3 days. The sample was collected by centrifugation at 5,500 rpm for 50 minutes and dried overnight at 37° C. to remove the solvent.

The α-CHC loading was achieved by soaking 250 mg of a solid metal-organic framework in 25 mL of methanol α-CHC solution (10 mg/mL) at room temperature under stirring for 1 day.

The DCA loading was achieved by soaking 250 mg of a solid metal-organic framework in 5 mL of methanol DCA solution (2 M) at room temperature under stirring.

The 5-FU loading was achieved by soaking 150 mg of a solid metal-organic framework in 5 mL of methanol DCA solution (7 mg/mL) at room temperature under stirring for 3 days.

In all cases (excluding loaded NU-1000 and loaded NU-901) the drug loaded metal-organic frameworks were collected by centrifugation at 5,500 rpm for 20 minutes, washed twice with methanol, centrifuged again for 10 minutes and dried overnight at 80° C. to remove the solvent. The loaded NU-1000 framework was collected by centrifugation at 5,500 rpm for 20 minutes and dried overnight at 37° C. to remove the solvent. The loaded NU-901 was collected by centrifugation at 5,500 rpm for 50 minutes and dried overnight at 37° C. to remove the solvent.

The siRNA-loaded samples were performed by soaking NU-1000 (around 110 mg) in deionized water (5.5 mL; DECP treated and sterile), which was made up to 100 μL with a solution of siRNA in deionized water (10 μM solution in deionized water; DECP treated and sterile). The solution was placed on an orbital agitator for mixing at 37° C. for 2 hours, after which the sample was removed and centrifuged at 3,500 rpm for 2 to 4 min. The supernatant was collected and stored for quantification of loading. The loaded framework was dried overnight at 37° C. Loading was determined using the Qubit method, as described below.

The amount of calcein adsorbed into a framework was quantified by using TGA. The amount of DCA adsorbed into a framework was quantified by ICP and TGA analysis. In the case of α-CHC and 5-FU, the amount of drug adsorbed into a framework was measured by UV-vis spectrophotometer at 337 and 266 nm, respectively, measuring the amount of drug present in the supernatant after the first centrifugation step. The loaded amount is given by the equation [1]:

$$\text{Loading (wt \%)} = \frac{\alpha\text{-}CHC_{added}\ (\text{mg})}{\alpha\text{-}CHC_{added}\ (\text{mg}) + MOF\ (\text{mg})} \qquad [1]$$

From these analyses the loading amounts for the various metal-organic framework was determined, and the loading amounts are given in Table 1 below:

TABLE 1

Loading levels (wt %) for drugs in the metal-organic frameworks (MOFs).

| MOF | Calcein (wt %) | DCA (wt %) | α-CHC (wt %) | 5-FU (wt %) |
|---|---|---|---|---|
| Zr-L1 | 4.9 | 43.0 | 31.0 | 1.6 |
| Zr-L2 | 1.0 | 40.6 | 3.1 | 2.9 |
| Zr-L3 | 1.0 | 41.8 | 5.0 | 1.1 |
| Zr-L4 | 1.2 | 61.7 | 7.2 | 2.7 |
| Zr-L5 | 2.1 | 53.4 | 14.8 | 2.4 |
| Zr-L6 | 15.2 | 53.6 | 20.3 | 2.5 |
| CAU-7 | NT | 33.0 | 9.3 | NT |
| NU-1000 | 4.3 | NT | NT | NT |

MOF Amorphization

Mechanical and temperature amorphization procedures were used to generate amorphous metal-organic frameworks holding components.

Mechanical Amorphization

In a typical experiment a loaded metal-organic framework (0.1 g) was placed in a stainless steel jar along with an 8 mm stainless steel ball. The jar was then oscillated at 20 Hz for 30 min using a Retsch MM200 mill to give the amorphous loaded metal-organic framework.

For the siRNA-loaded NU-1000 metal-organic framework and the calcein-loaded NU-901 metal-organic framework, the framework was placed in a stainless steel jar along with a 7 mm stainless steel ball. The jar was then oscillated at 20 Hz for 2 minutes using a Retsch MM200 mill to give the amorphous loaded metal-organic framework.

Thermal Amorphization

In a typical experiment (excluding loaded NU-1000) 40 mg of a loaded metal-organic framework was placed in a glass vial with a small amount of water, sufficient to wet the solids. Then, the sample was heated at 180° C. for 5 h.

For loaded NU-1000, the metal-organic framework compound was collected via centrifugation as described above, and then dried immediately for 24 h at 180° C. under vacuum.

Drug Delivery Assays

The drug delivery experiments were performed in an incubator at 37° C. with orbital agitation, using phosphate buffered saline (PBS, 10 mM) at pH 7.4 as the medium in order to simulate physiological conditions.

A loaded metal-organic framework (5 mg of loaded metal-organic framework for calcein-, α-CHC— and 5-FU-loaded frameworks, and 20 mg for DCA-loaded frameworks) was placed into a dialysis bag (MWCO 3500, Medicell International) with PBS (10 mL). Aliquots of PBS (1 mL) were removed for testing during the experiment, and replaced with fresh PBS (1 mL).

Alternatively, a loaded metal-organic framework (around 3-5 mg) was placed in an Eppendorf tube with 1 mL of PBS. Prior to the removal of a sample, the tube was centrifuged at 16,000 g for 50 s. The PBS solution was entirely removed from the tube for testing, and this was replaced with fresh PBS (1 mL).

The amount of drug released from a framework was determined from the amount of material present in the PBS samples taken at various time points during incubation. The samples were analysed by UV-vis spectroscopy with detection at 498 and 337 nm for calcein and α-CHC, respectively. In the case of DCA and 5-FU, the amount of drug released from the framework was measured by HPLC.

The corrected concentration of drug release, such as calcein is given by the equation [2]. Every experiment was performed by triplicate.

$$c_t = c'_t + \frac{v}{V} \sum_{0}^{t-1} c'_t \quad [2]$$

Figure 9:
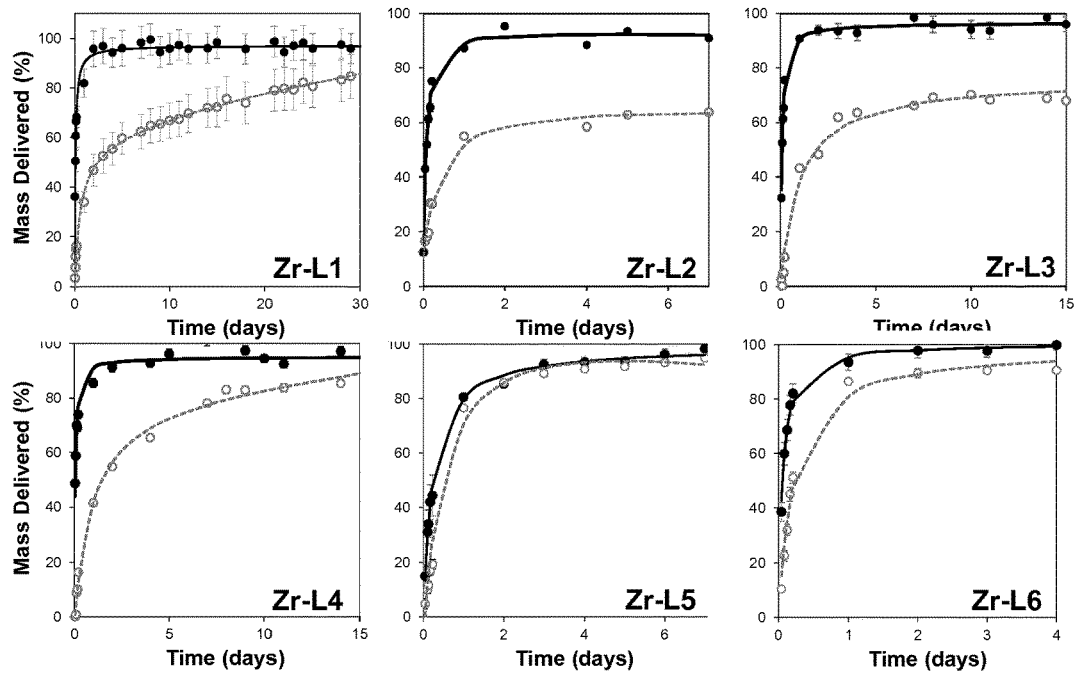
FIG. 9 shows the release profiles of calcein from crystalline (filled circles) and amorphous metal-organic frameworks (unfilled circles). Here, the amorphous metal-organic frameworks are prepared by mechanical amorphization. The release profiles show the amount of material released (%) over time (days), where the release amount is expressed with respect to the total amount of material releasable from the framework.

FIG. 9 shows the release profiles of calcein from crystalline (filled circles) and amorphous metal-organic frameworks (unfilled circles). Here, the amorphous metal-organic frameworks are prepared by mechanical amorphization.

Figure 13:
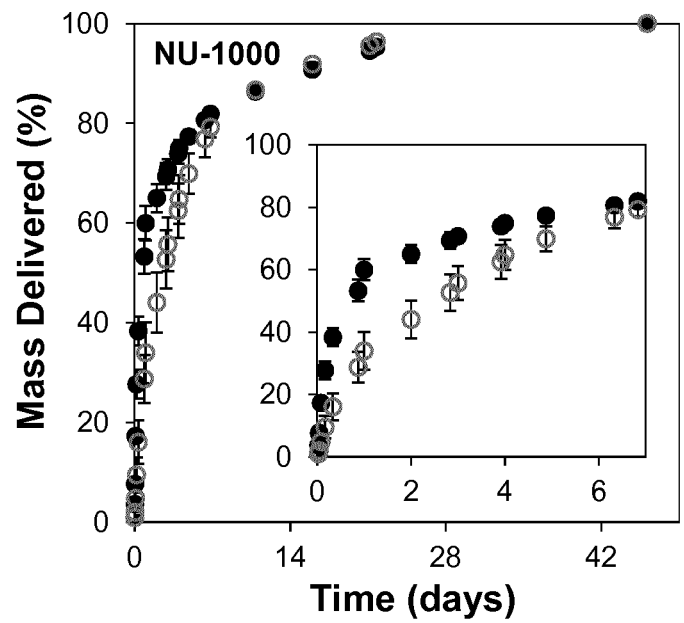
FIG. 13 shows the release profiles of calcein from crystalline (filled circles) and amorphous NU-1000 (unfilled circles). Here, the amorphous metal-organic frameworks are prepared by temperature amorphization. The release profiles show the amount of material released (%) over time (days), where the release amount is expressed with respect to the total amount of material releasable from the framework.

FIG. 13 shows the release profiles of calcein from crystalline (filled circles) and amorphous NU-1000 (unfilled circles). Here, the amorphous metal-organic frameworks are prepared by temperature amorphization.

Figure 14:
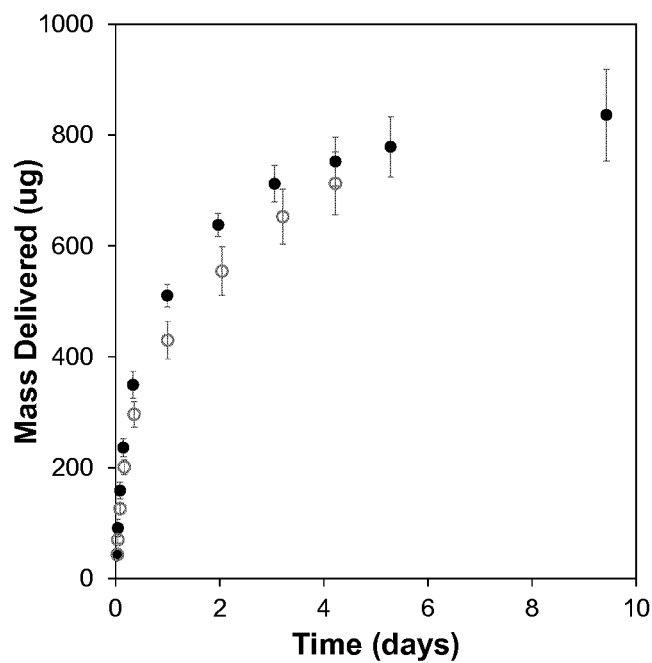
FIG. 14 shows the release profiles of calcein from crystalline (filled circles) and amorphous NU-901 (unfilled circles). Here, the amorphous metal-organic frameworks are prepared by mechanical amorphization. The release profiles show the amount of material released (%) over time (days), where the release amount is expressed with respect to the total amount of material releasable from the framework.

FIG. 14 shows the release profiles of calcein from crystalline (filled circles) and amorphous NU-901 (unfilled circles). Here, the amorphous metal-organic frameworks are prepared by mechanical amorphization.

Calcein was released from all the crystalline frameworks in approximately 2-3 days, which differed from release profiles for the amorphous frameworks.

For amorphous Zr-L2 and amorphous Zr-L3, 63% and 68%, calcein was released over 2 and 7 days respectively, indicating that the calcein was well trapped within the framework. In the case of amorphous Zr-L4, a slower and progressive release of calcein was observed over 15 days.

For the loaded Zr-L5 and Zr-L6 frameworks there was no significant difference between the release from the crystalline and amorphous forms. For frameworks with longer linkers, it is possible the porosity was not completely blocked during the ball-milling process, allowing the diffusion of guest molecules through the material.

The NU-1000 release profiles showed fully complete release around 50 days (c.a. 7 weeks) for both the crystalline and thermally amorphous forms. Over the initial first 6 days of release, the amorphous has a delayed release compared with the crystalline form.

For the release of calcein from NU-901 there is a noticeable and statistically significant difference, as per a two-way ANOVA test, between the release from the crystalline structure and mechanically amorphous structure. In a repeat experiment, the release of calcein from amorphous NU-901, when normalised to that of the earlier crystalline experiment was not significantly delayed compared with the release from the crystalline form. Further work is ongoing on this system. Nevertheless, it is clear that a sustained release of calcein from the amorphous framework, over a period of more than 6 days, is possible.

Figure 10:
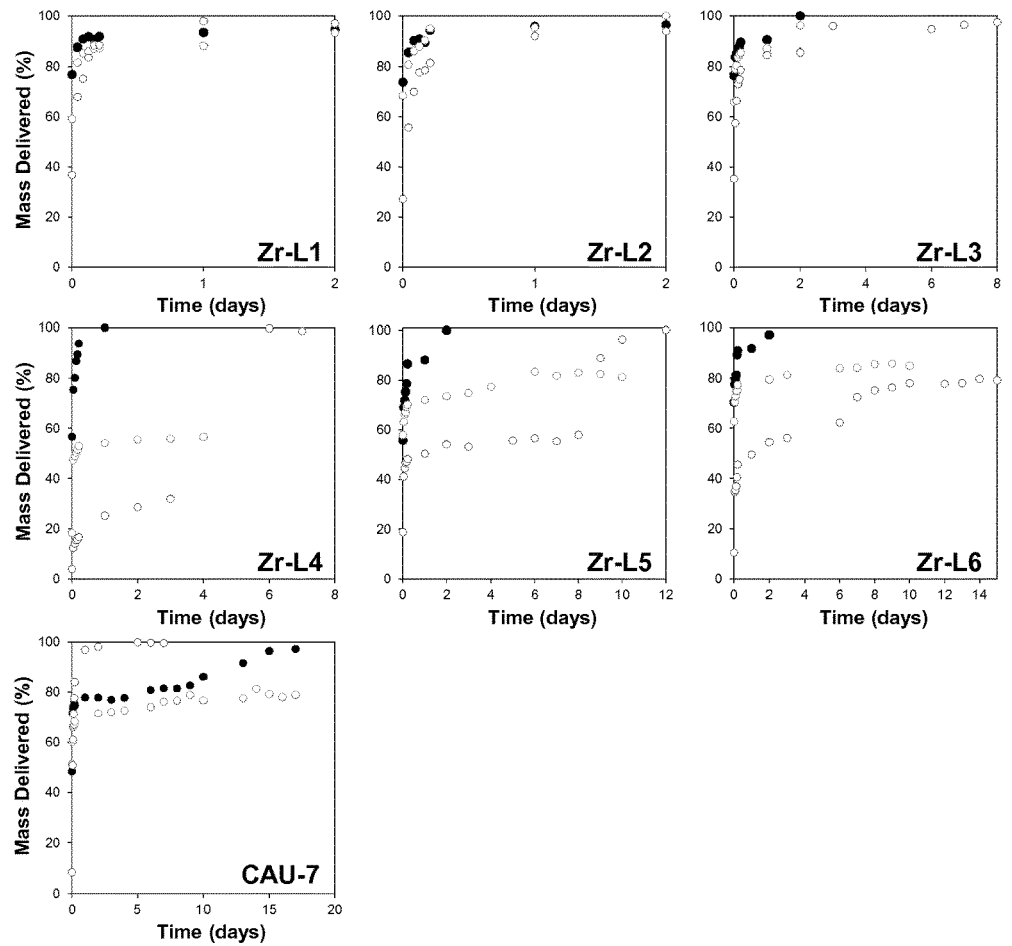
FIG. 10 shows the release profiles of DCA from crystalline and amorphous metal-organic frameworks. Here, the amorphous metal-organic frameworks are prepared by mechanical amorphization (red unfilled circles) or temperature amorphization (blue unfilled circles). The release profiles show the amount of material released (%) over time (days), where the release amount is expressed with respect to the total amount of material releasable from the framework.

FIG. 10 shows the release profiles of DCA from crystalline and amorphous metal-organic frameworks. Here, the amorphous metal-organic frameworks are prepared by mechanical amorphization (red unfilled circles) or temperature amorphization (blue unfilled circles).

DCA was delivered in 1 to 2 days from the crystalline Zr-based MOFs Zr-L1 to Zr-L6, and in around 2 days from the amorphous Zr-based MOFs Zr-L1 Zr-L2 and Zr-L3. After 3 or 4 days around 60% of the available drug was released from amorphous Zr-L4 and 80% from amorphous Zr-L5 and Zr-L6. For the thermally amorphous MOFs, differences in release profiled were observed between crystalline and amorphous forms for the Zr-L4 to Zr-L6 frameworks.

Finally, for CAU-7, DCA was completely delivered from the crystalline material in around 15 days, from the mechanically amorphous only 80% of DCA. Unusually, it was noted that complete release from the thermally amorphized CAU-7 framework was quicker than that of the crystalline form. This is thought to result from the use of water in the thermal amorphization, which may draw the drug from the framework during the treatment. It is also though that this may occur when the loading levels are very high (such as 33 wt % in this particular example).

Figure 11:
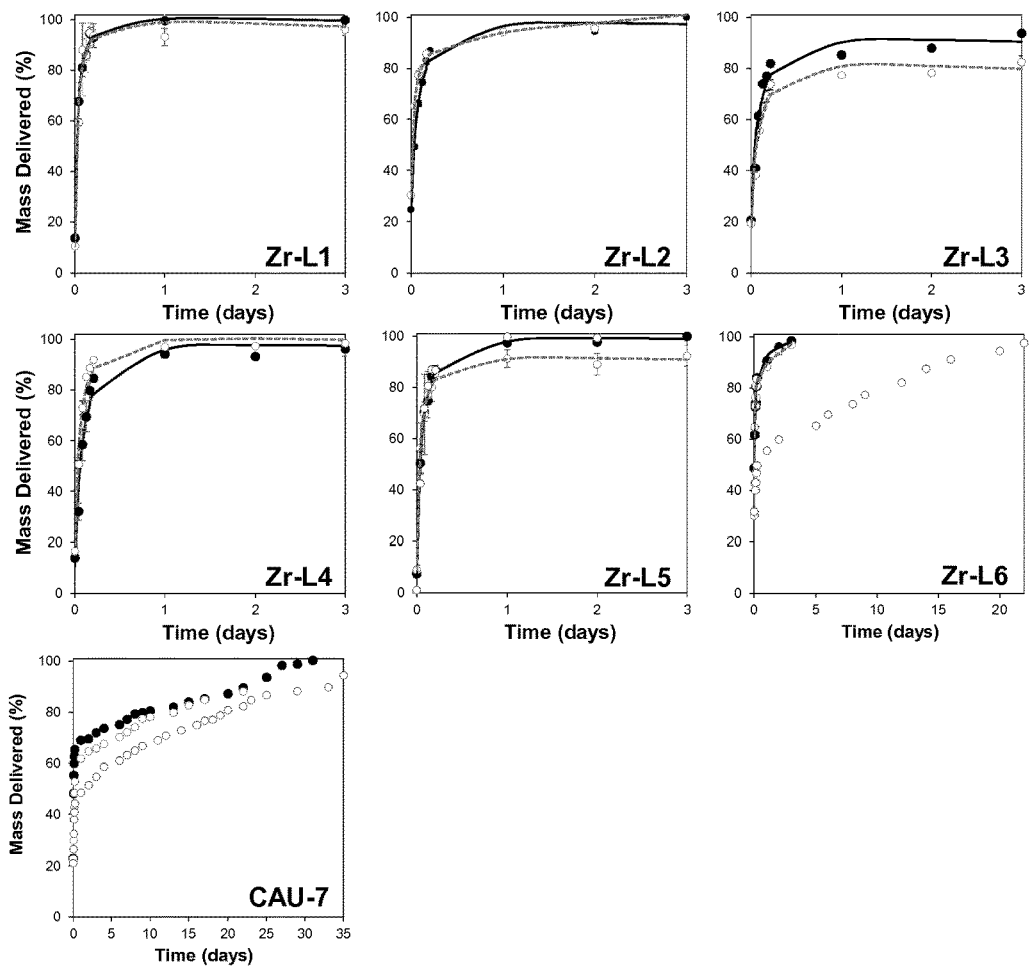
FIG. 11 shows the release profiles of α—CHC from crystalline and amorphous metal-organic frameworks. Here, the amorphous metal-organic frameworks are prepared by mechanical amorphization (red unfilled circles) or temperature amorphization (blue unfilled circles). The release profiles show the amount of material released (%) over time (days), where the release amount is expressed with respect to the total amount of material releasable from the framework.

FIG. 11 shows the release profiles of α-CHC from crystalline and amorphous metal-organic frameworks. Here, the amorphous metal-organic frameworks are prepared by mechanical amorphization (red unfilled circles) or temperature amorphization (blue unfilled circles).

α-CHC was completely delivered from the crystalline Zr-based MOFs Zr-L1 to Zr-L6 in around 1 to 3 days, except for Zr-L3, where the complete release of α-CHC had not yet been achieve after 3 days. Some differences in the release profiles between crystalline and mechanically amorphous frameworks were observed, but these differences were not significant difference.

From the temperature-based amorphous systems, amorphous Zr-L6 and CAU-7 were tested. The thermally amorphized frameworks exhibited delayed release with respect to the crystalline forms.

Figure 12:
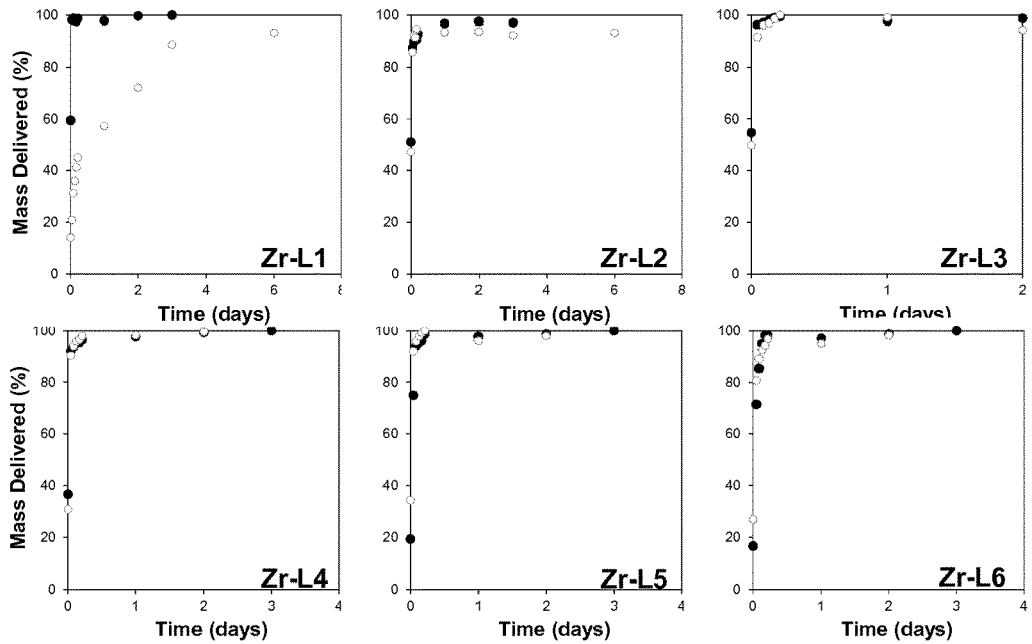
FIG. 12 shows the release profiles of 5-FU from crystalline and amorphous metal-organic frameworks. Here, the amorphous metal-organic frameworks are prepared by mechanical amorphization (red unfilled circles) or temperature amorphization (blue unfilled circles). The release profiles show the amount of material released (%) over time (days), where the release amount is expressed with respect to the total amount of material releasable from the framework.

FIG. 12 shows the release profiles of 5-FU from crystalline and amorphous metal-organic frameworks. Here, the amorphous metal-organic frameworks are prepared by mechanical amorphization (red unfilled circles) or temperature amorphization (blue unfilled circles).

5-FU was delivered in a maximum of 5 h from both the crystalline and amorphous metal-organic frameworks tested. The exception was Zr-L1, where there was a notable difference between the complete release from amorphous and crystalline forms (6 days for the former, 0.04 days for the latter).

The times for complete release of the drugs from the various metal-organic frameworks is summarised in Table 2.

TABLE 2

Release time, in days, for complete release of drugs from metal-organic frameworks, with comparison between crystalline/amorphous loaded forms, where the amorphous metal-organic frameworks are prepared by mechanical or temperature amorphization.

| | Complete Release Time (Days), Crystalline/Amorphous Drug | | | | | | |
|---|---|---|---|---|---|---|---|
| | Crystalline/Mechanical Amorphization | | | | Crystalline/Temperature Amorphization | | |
| MOF | Calcein | DCA | α-CHC | 5-FU | Calcein | DCA | α-CHC |
| Zr-L1 | 2/30 | 2/2 | 1/1 | 0.04/6 | NT | 2/2 | NT |
| Zr-L2 | $2/2_{63\%}$ | 2/2 | 1/1 | 0.21/0.21 | NT | 2/2 | NT |
| Zr-L3 | $2/7_{68\%}$ | 2/2 | $3_{94\%}/3_{82\%}$ | 0.21/0.21 | NT | 2/3 | NT |
| Zr-L4 | 2/15 | $1/3_{60\%}$ | 1/1 | 0.21/0.21 | NT | 2/7 | NT |
| Zr-L5 | 3/3 | $2/4_{80\%}$ | $1/3_{91\%}$ | 0.21/0.21 | NT | 2/12 | 1/1 |
| Zr-L6 | 2/2 | $2/3_{80\%}$ | 3/3 | 0.21/0.21 | NT | 2/10 | 3/22 |
| CAU-7 | NT | $17/17_{79\%}$ | 27/27 | NT | NT | 17/2 | 27/35 |
| NU-1000 | NT | NT | NT | NT | $1_{60\%}/7_{80\%}$ | NT | NT |

Where complete release is not observed in the time frame of the experiments, the amount released is given as a subscript to the day number when the amount was recorded. For example $2_{63\%}$ refers to 63% release at day 2.
NT refers to a system that has not yet been tested.

siRNA Delivery Assays

The siRNA delivery experiments were performed in an incubator at 37° C. with orbital agitation.

The siRNA-loaded NU-1000 experiments were performed in solutions of deionised water (DECP treated and sterile). All equipment was cleaned with RNAse Zap prior to use, in order to eliminate any potential degradation. Experiments were performed in triplicate.

A loaded amorphous framework (around 3-5 mg) was loaded into in an Eppendorf tube with deionised water (0.5 mL). Prior to the removal of a sample, the tube was centrifuged at 10,500×g for 1 min. Aliquots of solution (0.5 mL) were removed for testing at various time points during the experiment, and replaced with fresh deionised water (0.5 mL). Solutions were stored at −20° C. in a freezer until required in order to minimise any changes in the sample, including siRNA degradation. Sample solutions were purified using a Zymo Oligo Clean & Concentrator Kit to give a siRNA sample in deionised water with minimal amounts of NU-1000 linker, metal cluster, and other framework components.

The purified siRNA samples were analysed using the Qubit assay for the detection of oligonucleotides. A 1:200 mixture of the Qubit microRNA dye stock with the microRNA buffer was prepared. This mixture was then added into sample tubes together with aliquots of the siRNA sample (7 μL of sample made up to 200 μL with the mixture).

Each sample tube was vortexed after direct addition of the siRNA sample, and then allowed to sit for 2 min to allow the Qubit dye to bind to the siRNA. The samples were then measured on the Qubit Assay machine along with two siRNA standards (at 0 ng/mL and 500 ng/mL).

Figure 15:
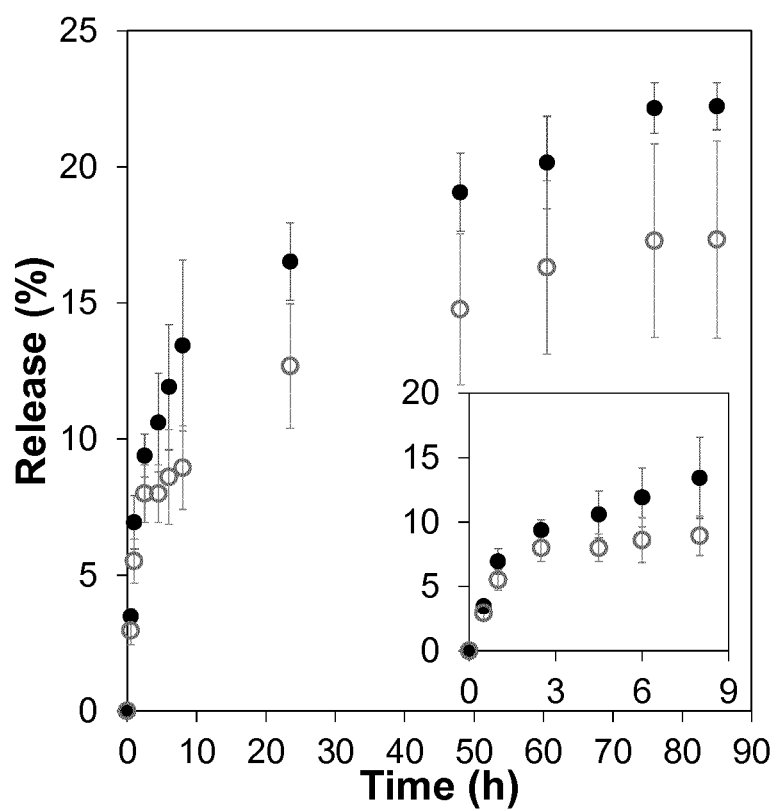
FIG. 15 shows the release profiles (% release over time, h) for the release of siRNA from crystalline (filled circles) and mechanically amorphous NU-1000 (unfilled circles), where the release amount is expressed with respect to the total amount of siRNA material releasable from the framework.

The release profiles of siRNA from crystalline and mechanically amorphous NU-1000 are shown in FIG. 15, including an inset expansion of the initial 9 hours of release The siRNA was releasable from crystalline and amorphised NU-1000 over a period of about 90 h. During this time, loaded crystalline NU-1000 released about 22% release of its total cargo, whereas the loaded amorphisised NU-1000 released about 17% of its cargo. These initial results demonstrate that the amorphization process is capable of delaying longer term siRNA release from a metal-organic framework. The release studies also showed that the amorphous form also lessened the initial burst release in the initial 9 hours of the release profile.

A similar siRNA release experiment performed by He et al. (*J. Am. Chem. Soc.* 2014, 136, 5181) in the same solvent (deionised water) and similar conditions was only quantified up to 8 hours where just under 20% of the siRNA loaded was released. The work of He et al. focusses on the use of crystalline forms of metal-organic frameworks, and there is no suggestion that amorphous forms could or would be useful for delivering components.

A two-way ANOVA was performed between the difference of the means for each sample time point, and it was determined that the two final time points for the crystalline system compared with the mechanically amorphous system were statistically significant with p-values <0.05.

Cell Culture

HeLa cells were prepared as described previously.

Cytotoxicity Assays

The effect of the metal-organic frameworks on cell vitality was determined by measuring metabolic activity, using either the MTS reduction assay or the Annexin V Assay.

The cytotoxicity assays were performed substantially as described above, using the MTS reduction assay (Promega, UK). The cytotoxicity activity of the crystalline Zr-containing metal-organic frameworks and the crystalline Bi-containing frameworks was investigated. These frameworks were not loaded with drugs.

The day before an experiment, HeLa cells were seeded in to a 96 well plate at a density of $5 \times 10^3$ cells per well. Prior to the treatments, the cells were washed twice with PBS. The metal-organic frameworks and α-CHC, both at varying concentrations, were dispersed in cell culture media. Then they were added to the cells and incubated for 24 h at 37° C. with 5% $CO_2$.

To measure toxicity, the cells were washed extensively to remove the solids, the media was replace with of fresh culture media (100 μL, containing 20 μl of MTS/phenazine methosulfate in a ration 20:1), and the plate was incubated for 75 min at 37° C. with 5% $CO_2$. The plates were visualized at 490 nm.

Annexin V staining experiments were also performed for the linker, $H_4$TBAPy. The day before an experiment, HeLa cells were seeded in to a 24 well plate at a density of 0.05×10⁶ cells per well. Prior to the treatments, the cells were washed twice with PBS. The linker compounds (L1 to L6 and $H_3BTB$), at varying concentrations, were dispersed in cell culture media. The resulting mixtures were then added to the cells and incubated for 24 h at 37° C. with 5% $CO_2$.

To measure the toxicity, the cells were washed extensively to remove the solids, the media was replaced with fresh culture media (without phenol red). Annexin V PE-Cy5 stain was added to each sample, and after 5 min the sample was placed in the cytometer with detection at 647 nm.

Figure 7:
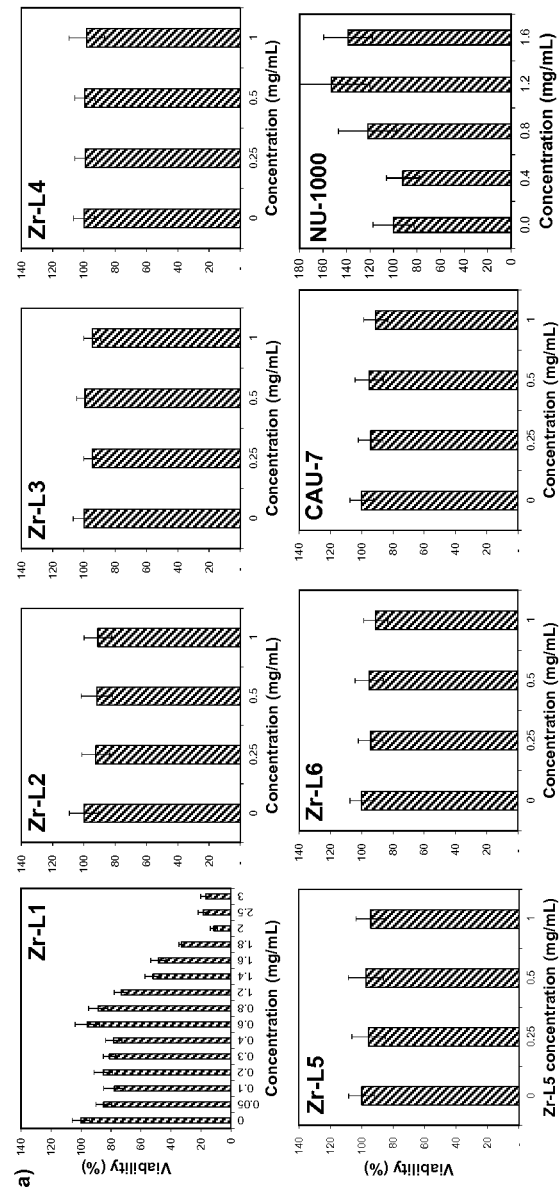
FIG. 7 shows the change in HELA cell viability (%) with the change in crystalline Zr-containing metal-organic framework concentration (mg/mL) in a MTS assay. The frameworks were not loaded with drug.
Figure 8:
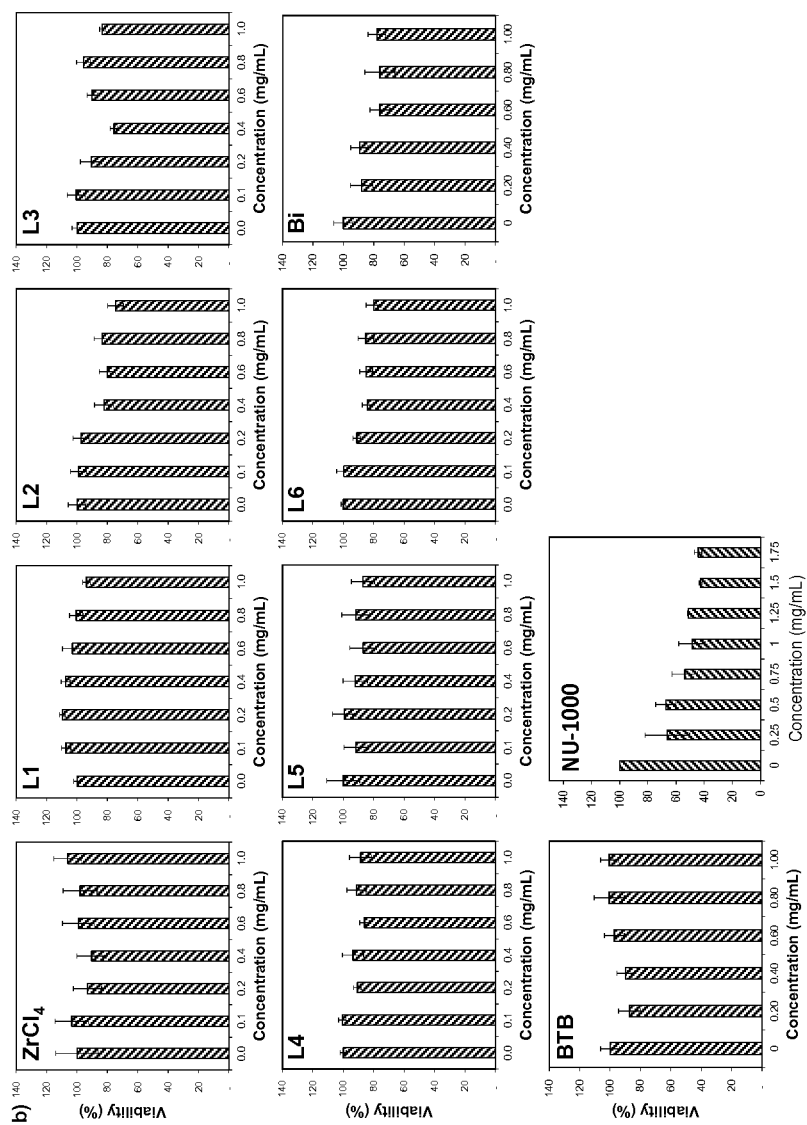
FIG. 8 shows the HELA cell viability (%) with the change in linker, $ZrCl_4$ and $Bi(NO_3)_3 \cdot 5H_2O$ concentration (mg/mL) in MTS assay (for Lx, $ZrCl_4$ and Bi) and Annexin V assay (for $H_4TBAPy$).

FIG. 7 shows the effects of various metal-organic frameworks on HeLa cell viability at a range of concentrations. FIG. 8 shows the effects of various ligands and Zr and Bi salts on HeLa cell viability at a range of concentrations. The Zr salt was $ZrCl_4$, and the Bi salts was $Bi(NO_3)_3 \cdot 5H_2O$. The ligands at those ligands mentioned in the synthesis section above.

All the metal-organic frameworks were biocompatible in the range of tested concentrations (up to 1 mg/mL). All the components used to prepare the metal-organic frameworks were also harmless to cells.

A cytotoxicity analysis on NU-901 was not performed. It is believed that there will be no significant difference between the behaviour of NU-1000 and NU-901, for example their interaction and uptake into cells, as they have a common linker, metal cluster, and have approximately the same particle size.

Drug Cellular Uptake

HeLa cells were seeded in a NUNC™ imaging four-well plate at a density of 1.11×10⁵ cell/mL and incubated for 24 h at 37° C. with 5% $CO_2$ in DMEM supplemented with 10% (v/v) Fetal Bovine Serum (FBS), 2 mM L-glutamine, 100 units/mL penicillin and 100 µg/mL streptomycin.

The cells were washed twice with PBS and incubated together with calcein-loaded crystalline Zr-containing metal-organic frameworks (0.5 mg/mL) for 24 h. The amorphous frameworks were obtained by mechanical amorphization of calcein-loaded crystalline Zr-containing metal-organic frameworks. The metal-organic frameworks were well-dispersed in culture media before they were added to the cells.

Untreated cell and free calcein (at a concentration of 0.075 mg/mL) were included as controls.

After incubation for 24 h, the cells were washed several times to remove the non-internalized particles. Cells then were incubated for 15 min with Hoechst 33342 (H33342) and 1× of CellMask™ Orange to stain the nucleus and cell membrane, respectively (each dye provided at a concentration of 5 µg/mL). The cells were then washed extensively to remove the dyes and fresh media (without phenol red) was added to each sample. Finally, the plate was placed on a Leica TCS SP5 confocal microscope for imaging. The microscope was equipped with 405 diode, argon and HeNe lasers. Leica LAS AF software was used to analyse the images.

Figure 16:
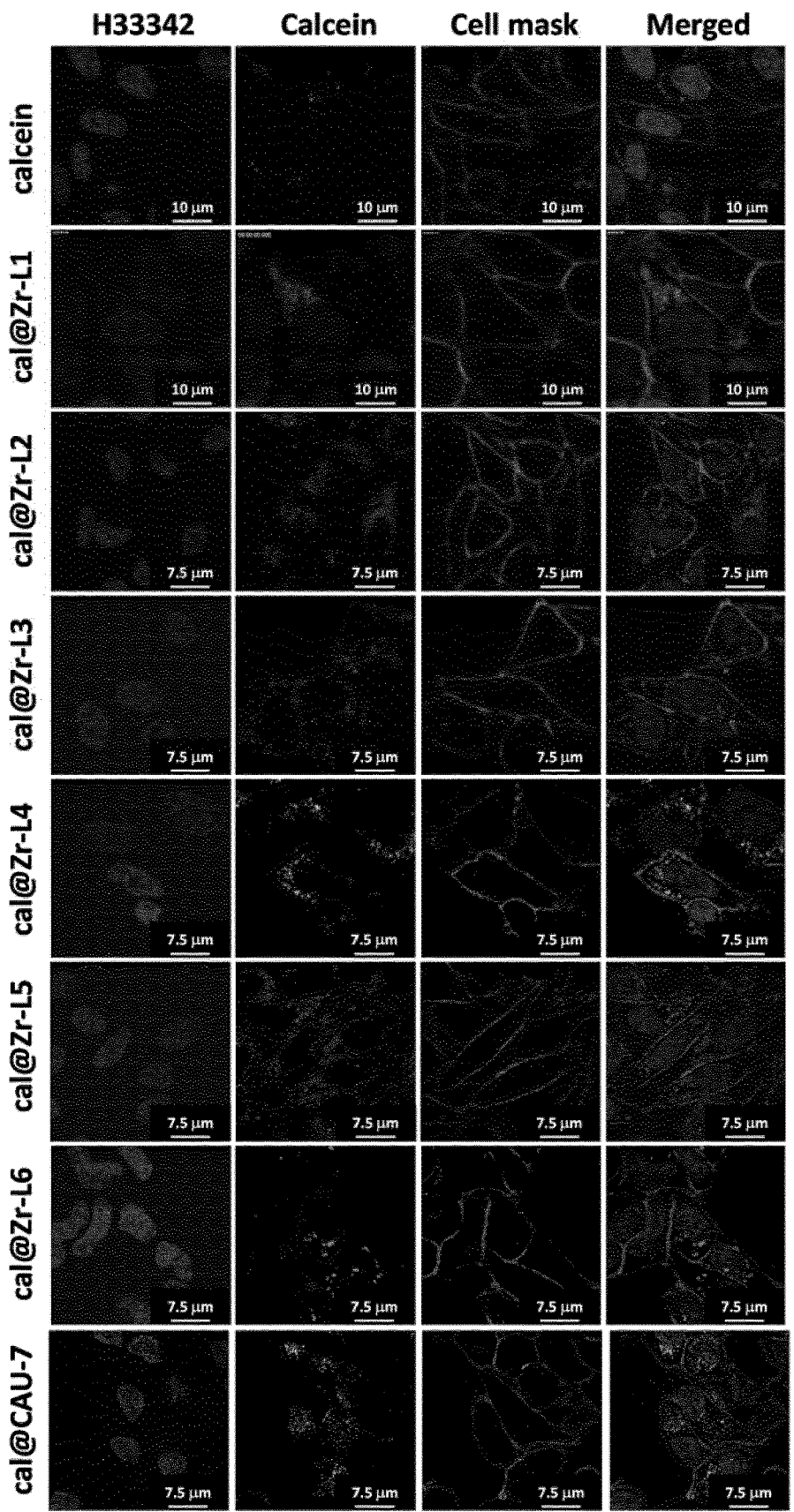
FIG. 16 is a series of confocal microscopy images of HeLa cells incubated for 24 h with crystalline calcein-loaded Zr-based metal-organic frameworks Zr-L1 to Zr-L6 and the calcein-loaded Bi-based metal-organic framework CAU-7. The cells were subsequently stained with Hoechst 33342 (5 μg/ml) and CellMask™ Orange (1×). The scale bar is 10 μm for the top two rows of images, and 7.5 μm for the remaining rows of images.

FIG. 16 shows the confocal microscopy images obtained from the uptake experiments.

Cells incubated with free calcein stained weakly in the form of bright vesicles at 24 h of incubation (see top row of images in FIG. 16), suggesting that calcein is encapsulated in endosomes. Although calcein is considered impermeable to the cell membrane, cellular uptake of impermeable dyes by endocytosis has been reported previously using Human Mesenchymal Stem Cells (MSCs) and the dye Lucifer yellow (LYCH) (see Oliver et al. and Orellana-Tavra et al.).

When the cells were incubated together with the amorphous calcein-loaded frameworks, a strong signal was detected after 24 h, confirming that the MOFs particles were successfully incorporated by cells. The punctate staining in the confocal images suggests MOF entrapment within intracellular vesicles. The MOFs are clearly inside the cells and not on the external part of the cell membrane: it is possible to visualise the cellular nucleus (blue), the MOF particles (green) and the periphery of the cells (red), confirming that the image is an internal plane of cells.

siRNA Cellular Uptake

HEK-293 cells were seeded in a 24 well Corning cell culture dish at a density of 1.6×10⁵ cell/mL and incubated for 24 h at 37° C. with 5% $CO_2$ in DMEM supplemented with 10% (v/v) Fetal Bovine Serum (FBS), 2 mM L-glutamine, 100 units/mL penicillin and 100 µg/mL streptomycin, 0.1 mg/mL hygromycin B, and 0.015 mg/mL blasticidin. The cells were then washed twice with PBS and incubated with the various conditions of siRNA. Negative controls were incubated with the DMEM medium.

Each well of a positive control was incubated with tagged siRNA (30 µmol) following the Lipofectamine RNAmax protocol from Thermo Fisher. Each well of Naked siRNA Tag was incubated with tagged siRNA (30 µmol).

Crystalline NU-1000 loaded with tagged siRNA was prepared according to the loading methods described above, in a scaled-down preparation. Typically NU-1000 (0.75 mg) was treated with a 10 µM stock of tagged siRNA (11.25 µL) and deionized water (26.25 µL; DECP treated and sterile). The amount of sample used in a well was in an amount to give approximately 30 µmol of the tagged siRNA per well.

After the 24 h incubation time, cells were washed twice to remove all non-internalized material. The cells were treated with trypsin (150 µL) for approximately 5 min, before complete media (described above, 350 µL) was added. The mixture was centrifuged at 1,200 rpm for 5 min to pellet the cells, and the supernatant was replaced with complete media lacking phenol red (250 µL).

Flow cytometry using $\lambda_{ex}$ set at 647 nm was performed. A gate was drawn around a population of negative HeLa cells which had not been not incubated with tagged siRNA, such that the gate count for subsequent samples was 10,000 events to ensure accuracy of data collection.

Figure 17:
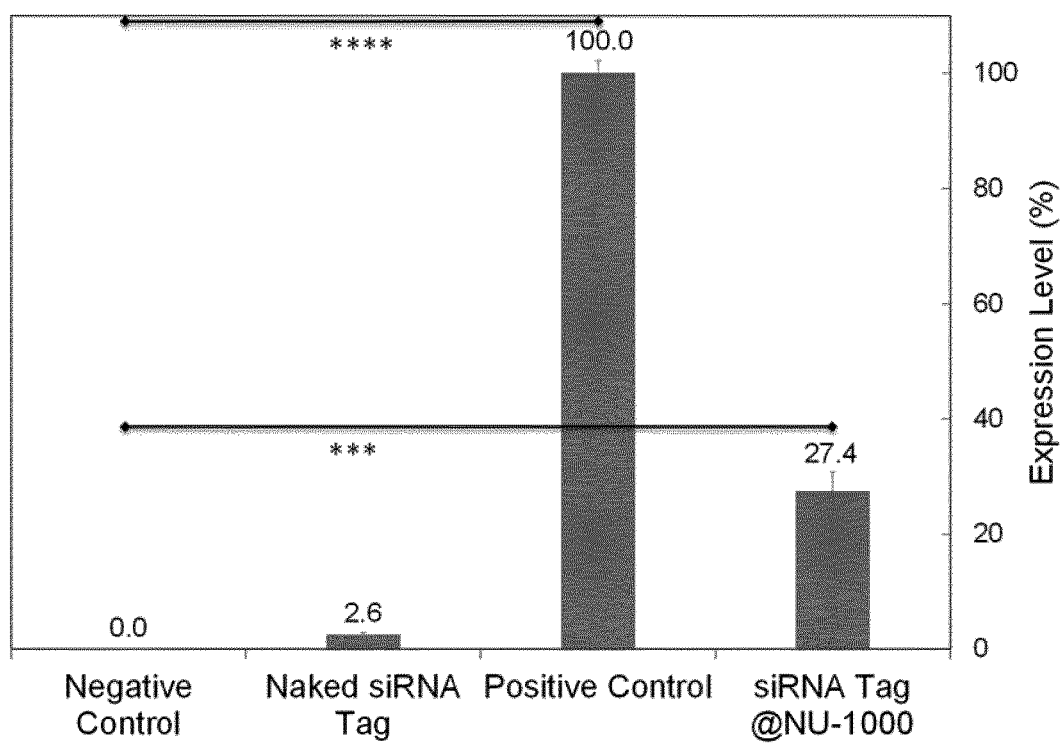
FIG. 17 shows the expression levels (%, with respect to positive control) for siRNA as determined by flow cytometry with detection at 647 nm, for a negative control (no siRNA), naked siRNA, positive control (siRNA loaded into lipofectamine) and loaded NU-1000 (siRNA loaded in crystalline NU-1000).

The expression levels in the flow cytometry indicating cellular uptake of the tagged siRNA are shown in FIG. 17. In the negative control there was no siRNA incubation, hence no incubation. The positive control contained siRNA loaded inside lipofectamine, a known cell entrant. This value was normalised to 100% expression to compare all other conditions to it. The naked siRNA Tag condition is pure, tagged siRNA incubated with cells. This siRNA is known to be degraded normally and does not cross the cell barrier due to its degradation by RNAses or other nucleases in the extracellular environment (see Whitehead et al. *Drug Discov.* 2009, 8, 129). There was no statistical significance between the level of expression from the negative control with no siRNA added and the naked siRNA.

The tagged siRNA loaded into the NU-1000 framework was detected inside the cell at a statistically significant expression level, as per one-way ANOVA, with a p-value <0.0002.

REFERENCES

All documents mentioned in this specification are incorporated herein by reference in their entirety.

C. Tamames-Tabar, D. Cunha, E. imbuluzqueta, F. Ragon C. Serre, M. J. Blanco-Prieto and P. Horcajada, *J. Mater. Chem. B* 2014, 2, 262.

M. J. Katz, Z. J. Brown, Y. J. Colón, P. W. Siu, K. a Scheidt, R. Q. Snurr, J. T. Hupp and O. K. Farha, *Chem. Commun.* 2013, 49, 9449-9451.

D. Cunha, C. Gaudin, I. Colinet, P. Horcajada, G. Maurin and C. Serre, *J. Mater. Chem. B* 2013, 1, 1101-1108.

J. H. Cavka, S. Jakobsen, U. Olsbye, N. Guillou, C. Lamberti, S. Bordiga and K. P. Lillerud, *J. Am. Chem. Soc.* 2008, 130, 13850-13851.

K. Shan, A. M. Lincoff, and J. B. Young, *Am. Coll. Physicians*, 1996, 125, 47.

R. Erttmann, N. Erb, A. Steinhoff, and G. Landbeck, *Cancer Res. Clin. Oncol.,* 1988, 114, 509.

L. Meng, X. Zhang, Q. Lu, Z. Fei, and P. J. Dyson, *Biomaterials*, 2012, 33, 1689.

S. Keskin and S. Kizilel, *Ind. Eng. Chem. Res.,* 2011, 50, 1799-1812.

P. Horcajada, R. Gref, T. Baati, P. K. Allan, G. Maurin, P. Couvreur, G. Férey, R. E. Morris, and C. Serre, *Chem. Rev.,* 2012, 112, 1232.

M. C. Bernini, D. Fairen-Jimenez, M. Pasinetti, A. J. Ramirez-Pastor, and R. Q. Snurr, *J. Mater. Chem. B,* 2014, 2, 766.

J. I. Jin-gou, Z. Jing-fen, H. A. O. Shi-lei, W. U. Dan-jun, L. I. U. Li, and X. U. Yi, 2012, 28, 166.

D. Cunha, M. Ben Yahia, S. Hall, S. R. Miller, H. Chevreau, E. Elka, G. Maurin, P. Horcajada, C. Serre, *Chem. Mater.* 2013, 25, 2767.

P. Horcajada, T. Chalati, C. Serre, B. Gillet, C. Sebrie, T. Baati, J. F. Eubank, D. Heurtaux, P. Clayette, C. Kreuz, J.-S. Chang, Y. K. Hwang, V. Marsaud, P.-N. Bories, L. Cynober, S. Gil, G. Férey, P. Couvreur, and R. Gref, *Nat. Mater.,* 2010, 9, 172.

A. C. McKinlay, B. Xiao, D. S. Wragg, P. S. Wheatley, I. L. Megson, and R. E. Morris, *J. Am. Chem. Soc.,* 2008, 130, 10440.

C. He, K. Lu, D. Liu, and W. Lin, *J. Am. Chem. Soc.,* 2014, 136, 5181.

T. D. Bennett, P. J. Saines, D. a Keen, J.-C. Tan, and A. K. Cheetham, *Chem.-Eur. J.,* 2013, 19, 7049.

P. Horcajada, R. Gref, T. Baati, P. K. Allan, G. Maurin, P. Couvreur, G. Férey, R. E. Morris, and C. Serre *Chem. Rev.* 2012, 112, 1232.

T. D. Bennett, P. Simoncic, S. A. Moggach, F. Gozzo, P. Macchi, D. A. Keen, J.-C. Tan and A. K. Cheetham, *Chem. Commun.* 2011, 47, 7983.

W. J. Rieter, K. M. Pott, K. M. Taylor and W. Lin, *J. Am. Chem. Soc.* 2008, 130, 11584.

K. W. Chapman, D. F. Sava, G. J. Halder, P. J. Chupas and T. M. Nenoff, *J. Am. Chem. Soc.* 2011, 133, 18583.

M. Giménez-Marqués, T. Hidalgo and C. S. O. Horcajada, *Coordination Chem. Rev.* 2016, 307, 342.

Y. Zhuo and C.-J. Liu, *Plasma Chem. Plasma Process* 2011, 31, 499.

J. E. Mondloch, W. Bury, D. Fairen-Jimenez, S. Kwon, E. J. Demarco, M. H. Weston, A. A. Sarjeant, S. T. Nguyen, P. C. Stair, R. Q. Snurr, O. K. Farha, J. T. Hupp, *J. Am. Chem. Soc.* 2013, 135, 10294.

C.-W. Kung, T. C. Wang, J. E. Mondloch, D. Fairen-Jimenez, D. M. Gardner, W. Bury, J. M. Klingsporn, J. C. Barnes, R. Van Duyne, J. F. Stoddart, M. R. Wasielewski, O. K. Farha, J. T. Hupp, *Chem. Mater.* 2013, 25, 5012.

K. A. Whitehead, R. Langer, D. G. Anderson, *Nat. Rev. Drug Discov.* 2009, 8, 129.

A. E. Oliver, K. Jamil, J. H. Crowe, F. Tablin, i Cell Preserv. Technol. 2004, 2, 35.

C. Orellana-Tavra, E. F. Baxter, T. Tian, T. D. Bennett, N. K. H. Slater, A. K. Cheetham, D. Fairen-Jimenez, *Chem. Commun.* 2015, 51, 13857.

The invention claimed is:

1. A method of delivering a component to a target location, the method comprising the steps of:
   (i) providing an amorphous metal-organic framework at a target location, wherein the amorphous metal-organic framework holds a component, wherein the component is an agrochemical, the component is not molecular iodine ($I_2$) and the component has a molecular weight that is at least 100; and
   (ii) permitting the release of the component from the amorphous metal-organic framework, thereby to provide the component at the target location.

2. An amorphous metal-organic framework holding a component, wherein the component is an agrochemical, the component is not molecular iodine ($I_2$) and the component has a molecular weight that is at least 100.

3. The amorphous metal-organic framework according to claim 2, wherein the metal-organic framework is a zirconium-containing metal-organic framework.

4. The amorphous metal-organic framework according to claim 3, wherein the zirconium-containing metal-organic framework has benzenedicarboxylate ligands.

5. The amorphous metal-organic framework according to claim 4, wherein the benzenedicarboxylate ligands are 1,4 benzenedicarboxylate ligands.

6. The amorphous metal-organic framework according to claim 2, wherein the metal-organic framework is UiO 66, NU-1000 or NU-901, such as UiO 66.

7. The amorphous metal-organic framework according to claim 2, wherein the metal-organic framework is a bismuth-containing metal-organic framework, such as wherein the metal-organic framework is CAU-7.

8. The amorphous metal-organic framework according to claim 2, wherein the component has:
   (i) three or more atoms; and/or
   (ii) one or more carbon atoms; and/or
   (iii) a molecular weight of at least 255.

9. The amorphous metal-organic framework according to claim 2, wherein the amorphous metal-organic framework is obtainable by amorphization of a crystalline metal-organic framework holding the component, such as wherein the amorphization is a ball milling of the crystalline metal-organic framework holding the component.

10. The method of claim 1, wherein the target location is within a cell, such as cell that is ex vivo.

11. The method of claim 1, wherein the step of providing the amorphous metal-organic framework at a target location includes passing the amorphous metal-organic framework through a cell wall, such as a eukaryotic cell wall.

12. The method of claim 1, wherein the amorphous metal-organic framework releases the component upon treatment with base, such as an aqueous basic solution, such as an aqueous basic solution at physiological pH.

13. The method of claim 1, wherein the component is released into an aqueous phase.

14. The method of claim 1, wherein:
(i) no more than 50% of the component is releasable or released from the amorphous metal-organic framework after 48 hours from initial release; and/or
(ii) at least 80% of the component is released or releasable from the amorphous metal-organic framework, such as at least 80% of the component is released or releasable from the amorphous metal-organic framework after 30 days from initial release.

15. The method of claim 1, wherein the metal-organic framework is a zirconium-containing metal-organic framework.

16. The method of claim 15, wherein the zirconium-containing metalorganic framework has benzenedicarboxylate ligands, such as wherein the benzenedicarboxylate ligands are 1,4-benzenedicarboxylate ligands.

17. The method of claim 1, wherein the metal-organic framework is UiO-66, NU-1000, or NU-901, such as UiO-66.

18. The method of claim 1, wherein the method is a method of treating a plant or a plant material.

19. The method of claim 1, wherein the agrochemical is a herbicide, insecticide, or fungicide.

20. The amorphous metal-organic framework of claim 2, wherein the agrochemical is a herbicide, insecticide, or fungicide.

* * * * *